(12) United States Patent
Kang et al.

(10) Patent No.: US 8,351,053 B2
(45) Date of Patent: Jan. 8, 2013

(54) APPARATUS AND METHOD FOR IN SITU TESTING OF MICROSCALE AND NANOSCALE SAMPLES

(75) Inventors: Wonmo Kang, Champaign, IL (US); M. Taher A. Saif, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 327 days.

(21) Appl. No.: 12/823,743

(22) Filed: Jun. 25, 2010

(65) Prior Publication Data

US 2011/0317157 A1    Dec. 29, 2011

(51) Int. Cl.
*G01B 11/14*    (2006.01)
(52) U.S. Cl. .................................................. 356/614
(58) Field of Classification Search .................. None
See application file for complete search history.

(56) References Cited

U.S. PATENT DOCUMENTS

| | | | |
|---|---|---|---|
| 4,784,720 A | 11/1988 | Douglas | |
| 4,855,017 A | 8/1989 | Douglas | |
| 5,501,893 A | 3/1996 | Laermer et al. | |
| 6,170,332 B1 | 1/2001 | MacDonald et al. | |
| 6,230,571 B1 | 5/2001 | Kimerer, Jr. | |
| 6,240,782 B1 | 6/2001 | Kato et al. | |
| 6,606,913 B1 | 8/2003 | Gianchandani | |
| 6,682,703 B2 * | 1/2004 | Micklash et al. | 506/40 |
| 6,817,255 B2 | 11/2004 | Haque et al. | |
| 7,451,596 B2 * | 11/2008 | Culpepper et al. | 60/527 |
| 7,752,916 B2 | 7/2010 | Han et al. | |

FOREIGN PATENT DOCUMENTS

DE     4241045     5/1994

OTHER PUBLICATIONS

Artz, E., Size Effects in Materials due to Microstructural and Dimensional Constraints: A Comparative Review, Acta Mater, 46, 5611-5626 (1998).
Badawi, K.F. et. al., Measuring thin film and multilayer elastic constants by coupling in situ tensile testing with x-ray diffraction, Appl. Phys. Lett., 80, 4705 (2002).
Behr, R. et al., TEM Investigation of the Superdislocations and their Interaction with Particles in Dispersion Strengthened Intermetallics, Intermetallics, 7, pp. 423-436, 1999.

(Continued)

*Primary Examiner* — Tu Nguyen
(74) *Attorney, Agent, or Firm* — Greer, Burns & Crain Ltd.

(57) ABSTRACT

According to example embodiments of the invention, a microscale testing stage comprises a frame having first and second opposing ends and first and second side beams, at least one deformable force sensor beam, a first longitudinal beam having a free end, a second longitudinal beam having a facing free end, a support structure, and a pair of slots disposed at each of the free ends. In certain embodiments, a separately fabricated microscale or nanoscale specimen comprises a central gauge length portion of a material to be tested, and first and second hinges providing a self-aligning mechanism for uniaxial loading. In other embodiments, a layer of a conductive material defines first and second conductive paths and an open circuit that can be closed by the specimen across the gap. In other embodiments, the stage is formed of a high melting temperature material.

8 Claims, 27 Drawing Sheets

OTHER PUBLICATIONS

Bohm, J. et. al., Tensile testing of ultrathin polycrystalline films: A synchrotron-based technique, Rev. Sci. Instrum., 75, 110 (2004).

Bonetti, E. et al., The influence of Grain Size on the Mechanical Properties of Nanocrystalline Aluminum, Nanostructured Materials, vol. 9, pp. 611-614, 1997.

Brenner, S.S., Tensile strength of whiskers, J. Appl. Phys., vol. 27, No. 12, pp. 1484-1491, 1956.

Brenner, S.S., Plastic deformation of copper and silver whiskers, J. Appl. Phys., vol. 28, No. 9, pp. 1023-1026,1957.

Brotzen, F.R., Mechanical Testing of Thin Films, International Materials Reviews, vol. 39, No. 1, pp. 24-45, 1994.

Chasiotis, I. et. al., A New Microtensile Tester for the Study of MEMS Materials with the Aid of Atomic Force Microscopy, Exp. Mech, 42, 51 (2002).

Chechenin, N.G. et al., Nanoindentation of Amorphous Aluminum Oxide Films III. The Influence of the Substrate on the Elastic Properties, Thin Solid Films, 304, pp. 70-77, 1997.

Chen, J.M. et al., Measuring the nonlinearity of silicon piezoresistance by tensile loading of a submicron diameter fiber using a microinstrument, Review of Scientific Instruments 75(1), 276-278 (2004).

Espinosa, H.D. et. al., A methodology for determining mechanical properties of freestanding thin films and MEMS materials, J. Phys. Solids, 51, 47 (2003).

Espinosa, H.D. et al., Plasticity size effects in free-standing submicron polycrystalline FCC films subjected to pure tension, Journal of the Mechanics and Physics of Solids, vol. 52, pp. 667-689, 2004.

Espinosa, H.D. et al., An interpretation of size-scale plasticity in geometrically confined systems, Proceedings of the National Academy of Sciences, vol. 102, No. 47, pp. 16933-16938, 2005.

Evoy, S. et al., Nanofabrication and electrostatic operation of single-crystal silicon paddle oscillators, Journal of Applied Physics, vol. 86, No. 11, pp. 6072-6077, 1999.

Fleck, N.A. et al., Strain gradient plasticity: Theory and experiment, Acta Metall. Mater., vol. 42, No. 2, pp. 475-487,1994.

Flinn, P.A. et. al., Measurement and Interpretation of Stress in Aluminum-Based Metallization as a Function of Thermal History, IEEE Trans. Electron Devices, ED-34, 689 (1987).

Gao, H. et al., Mechanism-based strain gradient plasticity—i. theory, J. Mech. Phys. Solids, vol. 47, No. 6, pp. 1239-1263, 1999.

Gibeling, J.C. et al., Observations of Anelastic Backflow Following Stress Reductions During Creep of Pure Metals, Acta Materialia, vol. 29, pp. 1769-1784, 1981.

Greek, S. et al., Micromechanical Tensile Testing, Materials Research Society Symposium Proceedings, vol. 436, pp. 227-232, 1997.

Greer, J.R. et al., Size dependence of mechanical properties of gold at the micron scale in the absence of strain gradients, Acta Materialia, vol. 53, No. 6, pp. 1821-1830, 2005.

Greer, J.R. et al., Comparing the strength of fcc and bcc sub-micrometer pillars: Compression experiments and dislocation dynamics simulations, Materials Science and Engineering A, vol. 493, No. 1-2, pp. 21-25, 2008.

Greer, J.R. et al, Nanoscale gold pillars strengthened through dislocation starvation, Phys. Rev. B: Condens. Matter, vol. 73, No. 24, pp. 2454101-2454106, 2006.

Gutkin, M.Y. et. al., Theoretical Models of Plastic Deformation Processes in Nanocrystalline Materials, Rev. Adv. Mater. Sci., 2, 80 (2001).

Hall, E.O., The deformation and ageing of mild steel: Iii discussion of results, Proc. Phys. Soc. London, Sect. B, vol. 64, pp. 747-753, 1951.

Han, X.D. et al., Low-Temperature In Situ Large-Strain Plasticity of Silicon Nanowires, Advanced Materials, 19(16), 2112-2112 (2007).

Han, J. et al., In situ microtensile stage for electromechanical characterization of nanoscale freestanding films, Review of Scientific Instruments, vol. 77, No. 4, pp. 45102-1-45102-8, 2006.

Han, J. et al., Novel mems apparatus for in situ thermo-mechanical tensile testing of materials at the micro- and nano-scale, Proceedings of the IEEE International Conference on Micro Electro Mechanical Systems (MEMS), p. 80-83, 2009, 22nd IEEE International Conference on Micro Electro Mechanical Systems, MEMS 2009.

Haque, M.A. et al., Microscale Materials Testing Using MEMS Actuators, Journal of Microelectromechancial Systems, vol. 10, No. 1, Mar. 2001, pp. 146-152.

Haque, M.A. et. al., In-situ Tensile Testing of Nano-scale Specimens in SEM and TEM, Experimental Mechanics, vol. 42, pp. 123-128 (2002).

Haque, M.A. et. al., A Review of MEMS-Based Microscale and Nanoscale Tensile and Bending Testing, Experimental Mechanics, vol. 43, No. 3, pp. 248-255, 2003.

Haque, M.A. et. al., Mechanical behavior of 30-50 nm thick aluminum films under uniaxial tension, Scr. Mater., 47, 863 (2002).

Haque, M.A. et. al., Application of MEMS force sensors for in situ mechanical characterization of nano-scale thin films in SEM and TEM, Sensors and Actuators A, vol. 97-98, pp. 239-245 (2002).

Haque, M.A. et. al., Deformation mechanisms in free-standing nanoscale thin films: A quantitative in situ transmission electron microscope study, Proceedings of the National Academy of Sciences, vol. 101, No. 17, pp. 6335-6340 (2004).

Haque, M.A. et. al., Thermo-mechanical properties of nano-scale freestanding aluminum films, Thin Solid Films, 484, 364 (2005).

Hattar, K. et. al., In situ transmission electron microscopy observations of toughening mechanisms in ultra-fine grained columnar aluminum thin films, J. Mater. Res., 20, 1869 (2005).

He, R. et al., Giant piezoresistance effect in silicon nanowires, Nature Nanotechnology 1(1), 42-46 (2006).

Hoffman, R.W., Nanomechanics of Thin Films: Emphasis: Tensile Properties, Mater. Res. Soc. Symp. Proc., 130, 295 (1989).

Huang, H. et al., Tensile Testing of Free-Standing Cu, Ag and Al Thin Films and Ag/Cu Multilayers, Acta Materialia, vol. 48, No. 12, pp. 3261-3269, 2000.

Hugo, R.C. et al., In-situ TEM tensile testing of DC magnetron sputtered and pulsed laser deposited Ni thin films, Acta Materialia, vol. 51, pp. 1937-1943, 2003.

Ikeda, T. et al., Tensile Testing of Single Crystal Silicon Thin Films at 800° C. using IR Heating. Solid-State Sensors, Actuators and Microsystems Conference, 2007.

Jackson, K.M. et. al., Mechanical Properties of Epitaxial 3C Silicon Carbide Thin Films, J. Microelectromech. Syst., 14, 664 (2005).

Kanda, Y., Piezoresistance effect of silicon, Sensors and Actuators A: Physical 28(2), 83-01 (1991).

Kang, Y.S. et al., Thickness Dependent Mechanical Behavior of Submicron Aluminum Films, Journal of Electronic Materials, vol. 26, No. 7, pp. 805-813, 1997.

Ke, T.S. et al., Structure of Cold-Worked Metals as Deduced from Anelastic Measurements, Symposium on Plastic Deformation of Crystalline Solids, Mellon Institute, Pittsburgh, pp. 185-192, 1950.

Kiener, D. et al., A further step towards an understanding of size-dependent crystal plasticity: In situ tension experiments of miniaturized single-crystal copper samples, Acta Materialia, vol. 56, No. 3, pp. 580-592, 2008.

Kim, J.-Y. et al., Size-dependent mechanical properties of molybdenum nanopillars, Applied Physics Letters, vol. 93, No. 10, pp. 101916-3, 2008.

Kizuka, T. et al., Measurements of the atomistic mechanics of single crystalline silicon wires of nanometer width, Physical Review B 72(3), 035333-035333 (2005).

Kraft, O. et. al., X-ray diffraction as a tool to study the mechanical behaviour of thin films, Mater. Sci. Eng., A, 288, 209 (2000).

Lee, B. et al., First-principles calculation of mechanical properties of Si(001) nanowires and comparison to nanomechanical theory, Physical Review B 75(19), 195328-13 (2007).

Legros, M. et al., Microsample tensile testing of nanocrystalline metals, Philosophical Magazine A, vol. 80, No. 4, pp. 1017-1026, 2000.

Li, X. et al., Ultrathin single-crystalline-silicon cantilever resonators: Fabrication technology and significant specimen size effect on Young's modulus, Applied Physics Letters 83(15), 3081-3083 (2003).

Maab, R. et al., Defect structure inn micropillars using x-ray microdiffraction, Applied Physics Letters, vol. 89, No. 15, pp. 151 905-3, 2006, 10, 1063/1.2358204.

Maab, R. et al., A strong micropillar containing a low angle grain boundary, Applied Physics Letters, vol. 91, No. 13, pp. 131 909-3, 2007, 10, 1063/1.2784938.

Matsuda, K., Nonlinear piezoresistance effects in silicon, Journal of Applied Physics. v 73. n 4. p. 1838-47. 1993.

McDowell, M.T. et al., On the Elastic Modulus of Metallic Nanowires, Nano Letters 8(11), 3613-3618 (2008).

Namazu, T. et al., Evaluation of size effect on mechanical properties of singlecrystal silicon by nanoscale bending test using AFM, J. Microelectromech. Syst., vol. 9, No. 4, pp. 450-459, 2000.

Neugebauer, C.A. et. al., Tensile Properties of Thin, Evaporated Gold Films, J. Appl. Phys., 31, 1096 (1960).

Nix, W.D. et al., Deformation at the nanonmeter and micrometer length scales: Effects of strain gradients and dislocation starvation, Thin Sold Films, vol. 515, No. 6, pp. 3152-3157, 2007.

Nix, W.D. et. al., Mechanical Properties of Thin Films, Trans A, 20A, 2217 (1989).

Rajagopalan, J. et al., Plastic deformation recovery in freestanding nanocrystalline aluminum and gold thin film, Science, vol. 315, No. 5820, pp. 1831-1831, 2007.

Read, D.T., Piezo-Actuated Microtensile Test Apparatus, American Society for Testing and Materials, vol. 26, No. 3, pp. 255-259 (1998).

Renault, P.O. et. al., Damage mode tensile testing of thin gold films on polyimide substrates by X-ray diffraction and atomic force microscopy, Thin Solid Films, 424, 267 (2003).

Robertson, I.M. et al., Application of In-Situ TEM Deformation Techniques to Observe how "Clean" and Doped Grain Boundaries Respond to Local Stress Concentrations, Ultramicroscopy, vol. 40, pp. 330-338, 1992.

Ruud, J.A., New method for tensile testing of thin films, Journal of Material Research, vol. 8, No. 1, pp. 112-117 (1993).

Sadeghian, H. et al., Characterizing size-dependent effective elastic modulus of silicon nanocantilevers using electrostatic pull-in instability, Applied Physic Letters 94(22), 221903-3 (2009).

Sanders, P.G. et al., Elastic and Tensile Behavior of Nanocrystalline Copper and Palladium, Acta Materialia, vol. 45, No. 10, pp. 4019-4025, 1997.

Senturia, S., Microsystem design, Boston. Kluwer Academic Publishers. 2001.

Sharpe, W.N. et al., A new technique for measuring the mechanical properties of thin films, Microelectromechanical Systems, Journal of, vol. 6, No. 3, pp. 193-199,1997.

Sharpe, W. et al., Fracture Strength of Single-Crystal Silicon Carbide Microspecimens at 24 (degree) C and 1000 (degree) C. IEEE/ASME Journal of Microelectromechanical Systems 17(1): 244-254, 2008.

Smith, C.S., Piezoresistance Effect in Germanium and Silicon, Physical Review 94(a), 42-42 (1954).

Spaepen, F. et al., Mechanical Properties of Thin Films & Multilayers, Current Opinion in Solid State and Materials Science, 1: 679-683, 1996.

Stolken, J.S. et al., A microbend test method for measuring the plasticity length scale, Acta Mater., vol. 46, No. 14, pp. 5109-5115, 1998.

Tang, W.C. et al., Laterally Driven Polysilicon Resonant Microstructures, Sensors and Actuators A, 20, pp. 25-32, 1989.

Teer, D.G. et. al., The Formation of Low Friction Wear-Resistant Surfaces on Titanium by Ion Plating, Thin Solid Films, 45, 583 (2001).

Timoshenko, A., Analysis of bi-metal thermostats, Journal of the Optical Society of America, 11 (3): 233-255, 1925.

Toriyama, T. et al., Single Crystal Silicon Nano-Wire Piezoresistors for Mechanical Sensors, Microelectromechanical Systems, Journal of 11(5), 605-611 (2002).

Tortonese, M. et al., Atomic resolution with an atomic force microscope using piezoresistive detection, Applied Physics Letters 62(8), 834-836 (1993).

Tsuchiya, T. et al., Cross comparison of thin-film tensile-testing methods examined using single-crystal silicon, polysilicon, nickel, and titanium films, J. Microelectromech. Syst., vol. 14, No. 5, pp. 1178-1186, 2005.

Tsuchiya, T. et. al., Specimen Size Effect on Tensile Strength of Surface-Micromachined Polycrystalline Silicon Thin Films, J. Microelectromech. Syst., 7, 106 (1998).

Uchic, M.D. et al., A methodology to investigate size scale effects in crystalline plasticity using uniaxial compression testing, Materials Science & Engineering A, vol. 400-401, pp. 268-278, 2005.

Uchic, M.D. et al., 3D microstructural characterization of nickel superalloys via serial-sectioning using a dual beam FIB-SEM, Scripta Materialia, vol. 55, No. 1, pp. 23-28. 2006.

Uchic, M.D. et al., Sample dimensions influence strength and crystal plasticity, Science, vol. 305, No. 5686, pp. 986-989, 2004.

Xiang, Y. et. al., Plane-strain bulge test for thin films, J. Mater. Res., 20, 2360 (2005).

Yi, S. H. et al., Electroless Nickel Films: Properties and Fabricated Cavity Structure, Journal of Microelectromechanical Systems, vol. 11, No. 4, pp. 293-301, 2002.

Yi, T. et al., Microscale material testing of single crystalline silicon: process effects on surface morphology and tensile strength, Sens. Actuators, A, vol. 83, No. 1-3, pp. 172-178,2000.

Yu, D.Y.W., The yield strength of thin copper films on Kapton, J. Appl. Phys., 95, 2991 (2004).

Yuan, B., Mechanical Testing of Polysilicon Thin Films with the ISDG, Exp. Mech., 21, 32 (1997).

Zhang, Y. et al., Direct Observation of Super-Plasticity of Best-SiC Nanowires at Low Temperature, Advanced Functional Materials 17(17), 3435-3440 (2007).

Zupan, M. et al., Development of high-temperature microsample testing, Experimental Mechanics 41(3): 242-247, 2001.

Zupan, M. et al., High temperature microsample tensile testing of gamma-TiAl, Materials Science and Engineering a—Structural Materials Properties Microstructure and Processing 319: 810-814, 2001.

* cited by examiner

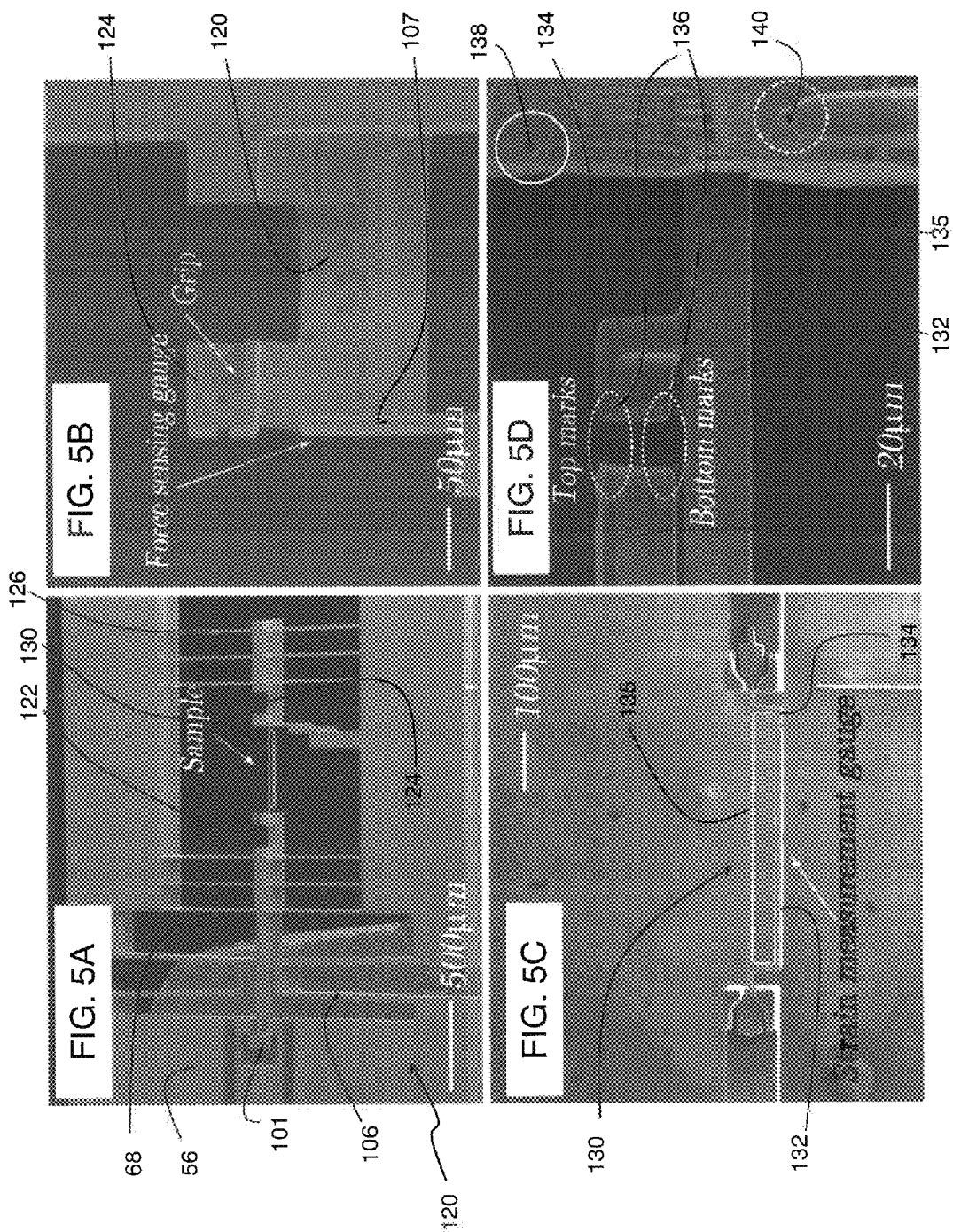

Case I

Case II

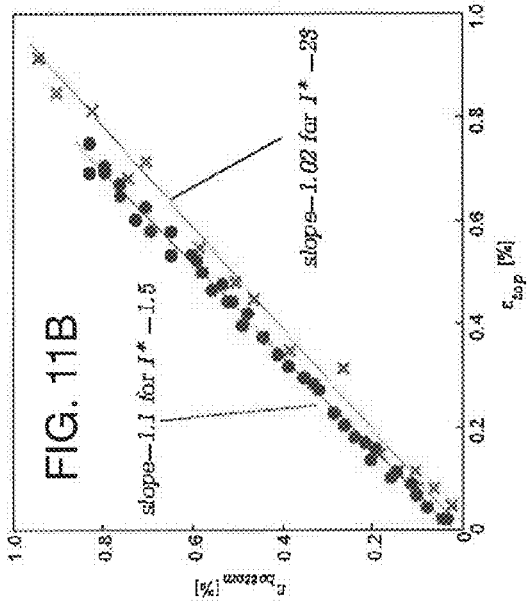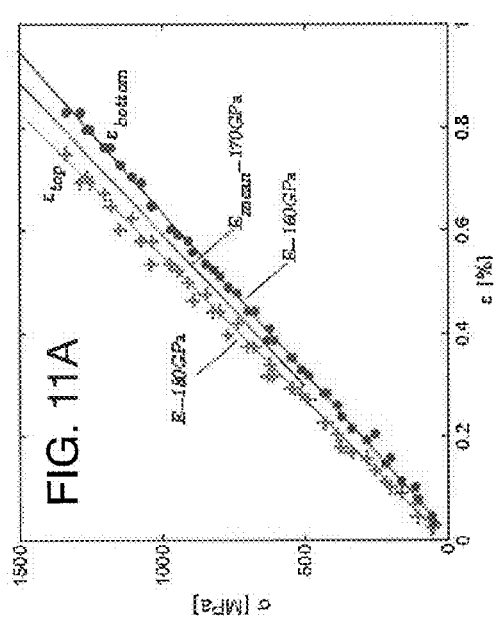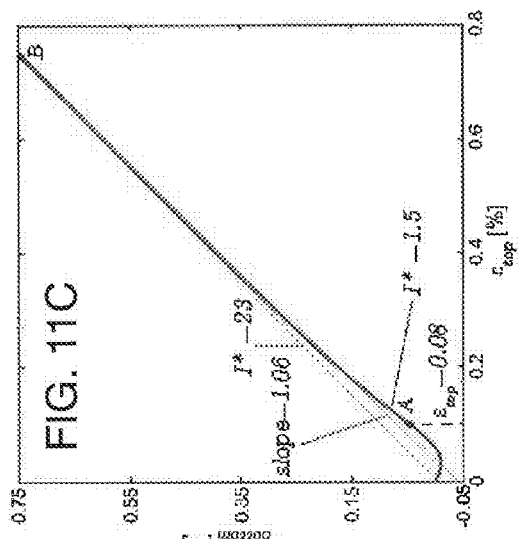
FIG. 11A
FIG. 11B
FIG. 11C

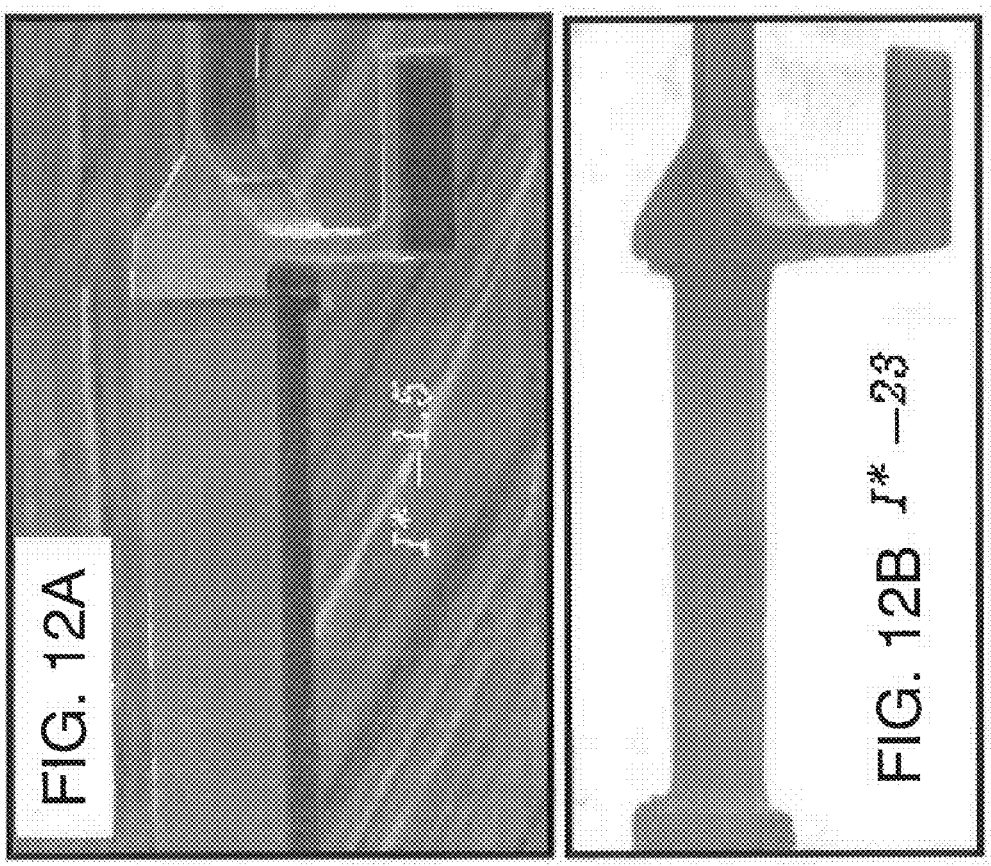

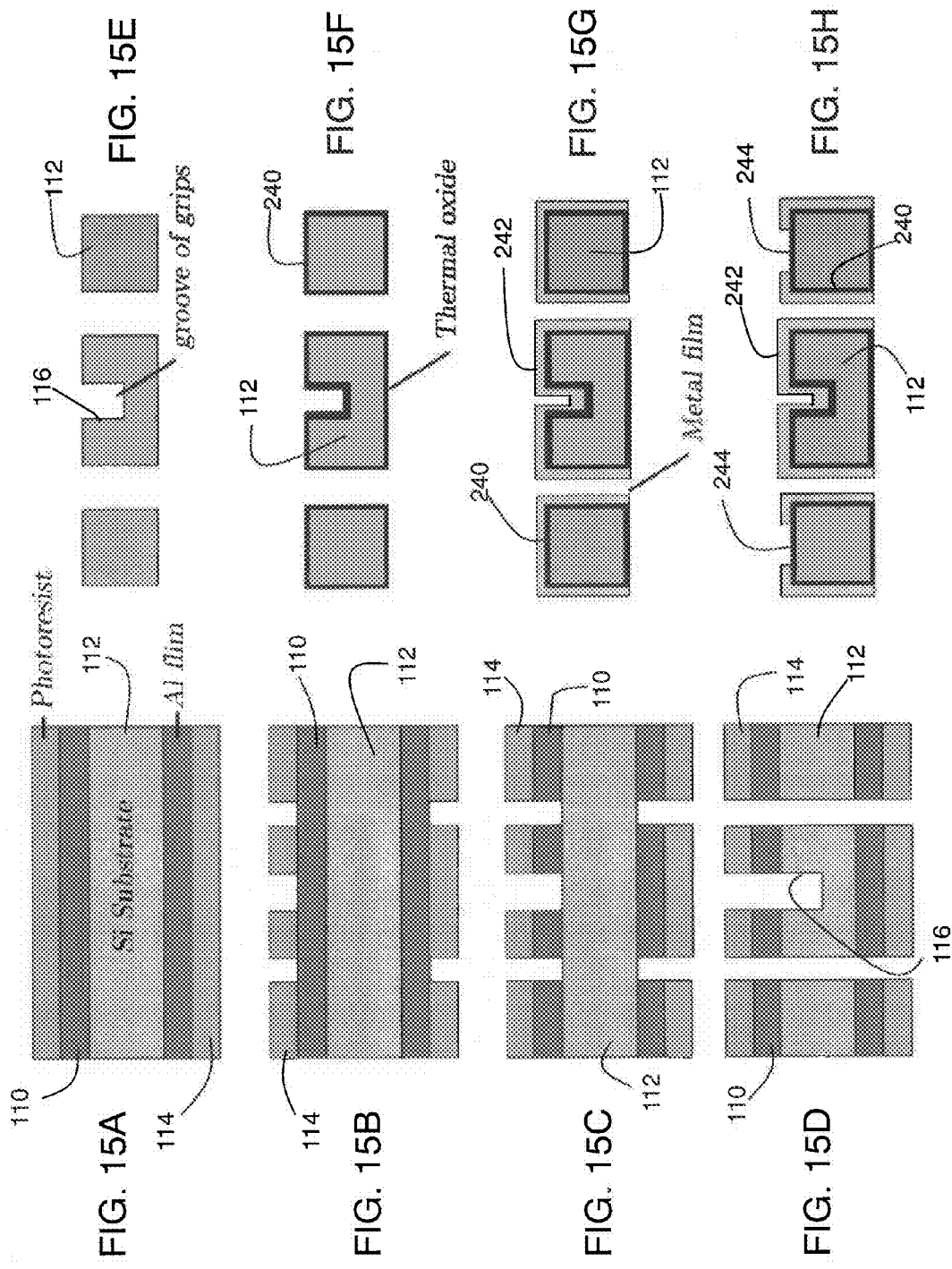

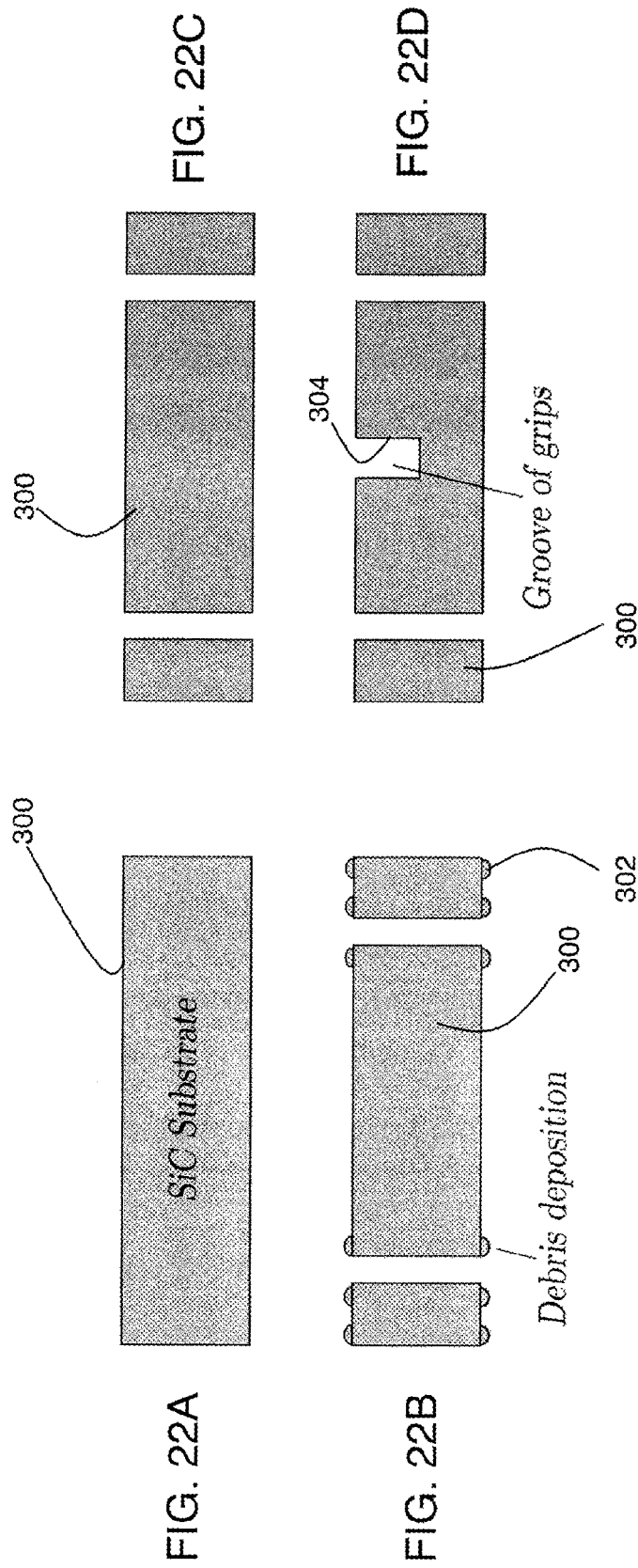

APPARATUS AND METHOD FOR IN SITU TESTING OF MICROSCALE AND NANOSCALE SAMPLES

STATEMENT OF GOVERNMENT INTEREST

This invention was made with Government assistance under Grant No. CMMI 07-28189 awarded by National Science Foundation. The Government has certain rights in the invention.

FIELD OF THE INVENTION

A field of the invention is material testing of microscale and nanoscale samples.

BACKGROUND OF THE INVENTION

As part of applications such as micro-electronic and micro-electromechanical systems (MEMS), nano-electromechanical systems (NEMS), and bio-MEMS, microscale and nanoscale materials exhibit mechanical properties and deformation mechanisms that are different from their bulk counterparts. Accurately predicting material response requires understanding fundamental mechanisms of material deformation and fracture occurrence in microscale and nanoscale. Material properties typically cannot be extrapolated from their respective bulk values, since material behavior often is not only different in microscale and nanoscale, but is also significantly affected by microstructure, sample size, and/or fabrication processes, and further is very sensitive to the influences of interfaces and adjoining materials. Changes in grain size and sample texture can lead to different responses even for the same materials. Some deformation mechanisms that are unimportant at bulk scale can become dominant as the sample's volume decreases and the relative surface area increases, such as in thin films. Samples made by gas deposition may exhibit different characteristics from those obtained by chemical clustering. Samples fabricated by mechanical attrition of metal powders may behave differently than those segmented from bulk materials.

Experiments to determine mechanical behavior and deformation mechanisms at macroscale have been largely successful. Yet, as the need for using smaller-scale materials has increased, such as with the development of microelectronics and micro-sensors, it has become increasingly important to assess the mechanisms of deformation and failure of materials at microscale and nanoscale. However, due to the limited number of available testing techniques for microscale and nanoscale samples, characterizing materials at these small scales has been a challenge, and much effort has been put into developing apparatus and methods for testing.

In general, the tension test is the most extensively developed and widely used test for material behavior, and it can be used to determine nearly all aspects of the mechanical behavior of a material. The basic principle of the tension test is quite simple, but numerous variables affect results. General sources of variation in mechanical-test results include factors such as shape of the specimen being tested, method of gripping the specimen, method of applying the force, speed of elongation, etc. Also, the extent of deformation in tension testing is limited by necking.

Compression tests are alternative approaches that overcome the necking limitation. Compression tests can provide useful information on plastic deformation and failure, but certain precautions must be taken to assure a valid test of material behavior. A buckling mode occurs when the length-to-diameter (L/D) ratio of the test specimen is large. In addition, even slightly eccentric loading on nonparallel compression plates will lead to shear distortion. Therefore, small L/D ratios are normally desired to avoid buckling and provide accurate measurements of the deformation behavior of materials in compression. Friction is another source of anomalous deformation in compression testing of ductile materials.

At macroscale, uniaxial tension and compression tests are accomplished by gripping opposite ends of a test item within the load frame of a test instrument, and producing tension in the specimen along a single axis while measuring the specimen's response. When properly conducted, such tests provide force-deformation relations that can quantify several important mechanical properties of a material such as 1) elastic deformation properties (Young's modulus and Poisson's ratio), 2) yield strength and ultimate tensile strength, 3) ductility properties, and 4) strain-hardening characteristics. Consideration of these material characteristics is important for reliable and optimized design.

In situ uniaxial tests, such as in scanning electron microscope (SEM) or transmission electron microscope (TEM) chambers, can potentially be used to allow direct observation of the deformation mechanism for quantitative and qualitative analysis. In the microscale or nanoscale, however, certain challenges arise when loading specimens. Examples include gripping of the specimen, aligning of the specimen in the direction of the force (to minimize likelihood of invalidation of the test caused by flexural stress on the specimen and resultant premature failure), and generating small forces (e.g., on the order of micro-Newtons) with high resolutions.

Some of these challenges can be addressed by using a substrate layer that is usually very compliant and with known material properties along with the actual specimen to be tested. However, introduction of the substrate complicates the experimental analysis because the microscale material properties of the substrate itself may not be known accurately, and because the interface with the substrate may influence the mechanical behavior of the specimen.

For example, a prior method of fabricating freestanding aluminum films includes evaporating metal film on a glass slide covered with a water-soluble layer, releasing the thin film from the glass slide by immersing it in water, and gluing the film to grips of a nano-tensilometer with epoxy. However, problems of mounting the specimen and premature specimen failure invalidate a significant number of tests using this method, and experimental results from the tests have shown significant variation in measured elastic modulus and ultimate tensile strength.

Another prior fabrication technique includes sputtering metal film on glass slides and releasing the films by peeling the films off from a substrate. A motor-driven micrometer is used to produce elongation in the films, and a load cell is used to read the stress. Laser spots diffracted from the gratings on the specimen surface determine the strain with 0.002% resolution.

Yet another known method provides a piezoactuated tensile testing apparatus using Ti—Cu—Ti multilayer films with a length of 700 μm, a width of 200 μm, and a total thickness of 1.2 μm. The films are patterned on wafers by lithography, and are then released from the substrate by wet etching of the substrate. Such a tensile testing apparatus has been known to provide force and displacement resolutions of about 200 μN and 20 nm, respectively. Still another testing method uses piezoelectric actuators for displacement with a load cell, a laser interferometer, and a strain gauge-optical encoder assembly to measure force and displacement.

A more recent material testing method is disclosed in U.S. Pat. No. 6,817,255, issued Nov. 16, 2004 (the '255 patent) to Haque and Saif, which is incorporated in its entirety herein by reference. The '255 patent discloses an apparatus and method for uniaxial tensile testing of a thin film material. This apparatus allows quantitative study of thin metal films down to very small thicknesses. The compact size and displacement-based measurement of example devices in the '255 patent allows one to conduct in-situ quantitative and qualitative tensile testing in environments such as a TEM and an SEM.

An example apparatus disclosed in the '255 patent includes a testing stage (e.g., a compact MEMS-based chip) that includes a co-fabricated thin film specimen to be tested, held by at least one force sensor beam at a first longitudinal end and by a support structure at a second longitudinal end. An example support structure includes a longitudinal beam connected to the second longitudinal end and aligned with the tensile axis of the specimen, and a plurality of lateral support beams. The support beams reduce flexing of the specimen resulting from misalignment of the pulling direction with the tensile axis of the specimen. Preferred embodiments of the chip include a pair of structural springs fabricated for maintaining structural integrity between the first and second ends of the chip and for addressing misalignment. Markers (e.g., displacement gauges) may be provided for measuring displacement of longitudinal ends of the specimen and deflection of the force sensor beam.

To test the thin film sample (specimen), the ends of the stage are separated (e.g., pulled) from one another by an actuator, such as a piezoactuator in SEM or a motor in TEM, which provides a tensile load on the sample. Measured displacement is used to determine material properties of the thin film specimen. For example, the force on the sample is determined from the displacement and the spring constant of the force sensor beams(s). The spring constant may be determined mathematically given dimensions and properties of the force sensor beams and/or by calibration, such as by using a nanoindenter. Sample stretching may be measured, for instance, by measuring displacement of the force sensor beams and the support structure.

Another testing stage for testing thin film samples is disclosed in Han, J. and Saif, M. T. A., "In Situ microtensile stage for electromechanical characterization of nanoscale freestanding films", Review of Scientific Instruments, Vol. 77, No. 4, pp. 45102-1-8, 2006 ("Han and Saif"), which is incorporated in its entirety herein by reference. An example embodiment disclosed in Han and Saif uses a testing stage co-fabricated with a thin film specimen, as with the '255 patent. The specimen is disposed between a support structure with a longitudinal beam axially aligned with a tensile axis and a plurality of lateral beams at one end, and by one or more deformable, lateral force sensor beams with a bisecting longitudinal beam at the opposite end. To protect the metal thin film sample from possible premature failure during fabrication of the testing stage, a protecting beam is provided. The protecting beam extends parallel to the co-fabricated sample and connects the support structure to the longitudinal beam bisecting the force sensor beams.

After fabricating the sample, the protecting beam is cut using focused ion beam (FIB) to provide a displacement gauge. A laterally extending beam disposed between the support structure and the force sensor beams provides a reference displacement gauge. Tensile testing is performed similarly to that described in the '255 patent. The displacement gauges measure displacement of the sample and the force sensor beams, and they are sufficiently near the sample to allow simultaneous observation of the sample stress-strain and the displacement gauges in an observation chamber.

U.S. patent application Ser. No. 11/897,927 to Han et al., filed Aug. 31, 2007, incorporated in its entirety herein by reference, discloses methods and apparatus for testing a microscale or nanoscale sample using an assembly approach, which allows a sample to be fabricated independently of the testing stage. A testing stage comprises a frame having first and second laterally opposing ends, first and second side beams, and first and second longitudinal beams. Each of a pair of slots disposed at each of the free ends of the first and second longitudinal beams comprises a tapered portion leading to a generally longitudinal portion. The slots provide a seat for a dogbone-shaped sample.

SUMMARY OF THE INVENTION

According to example embodiments of the invention, a microscale testing stage comprises a frame having first and second opposing ends and first and second side beams. At least one deformable force sensor beam near the first end extends laterally across the frame between the first and second side beams. A first longitudinal beam bisects the at least one force sensor beam and has a free end, and a second longitudinal beam has a free end facing the free end of the first longitudinal beam to define a gap therebetween. A support structure is disposed near the second end. A pair of slots is disposed at each of the free ends of the first and second longitudinal beams, respectively. A separately fabricated microscale or nanoscale specimen comprises a central gauge length portion of a material to be tested, first hinges disposed at each of opposing longitudinal sides of the gauge length portion, and second hinges disposed at each of opposing longitudinal sides of the first hinges, wherein the first hinges are disposed between the second hinges and the gauge length portion. Opposing ends of the specimen are provided for inserting into each of the pair of slots, respectively. The first hinges and the second hinges provide a self-aligning mechanism for uniaxial loading. In particular example embodiments, the slots have a depth that is about half of the thickness of the stage to reduce misalignment.

According to another embodiment of the present invention, a microscale testing stage comprises a frame having first and second opposing ends and first and second side beams. At least one deformable force sensor beam near the first end extends laterally across the frame between the first and second side beams. A first longitudinal beam bisects the at least one force sensor beam and has a free end, and a second longitudinal beam has a free end facing the free end of the first longitudinal beam to define a gap therebetween. A support structure is disposed near the second end. A pair of slots are disposed at each of the free ends of the first and second longitudinal beams, respectively, and each of the slots provide a seat for an end of a separately fabricated microscale or nanoscale specimen. A conductive layer of a conductive material is disposed on or in the stage, and defines a first conductive path through at least a portion of the stage from a first contact on the stage to one of the slots and a second conductive path through at least another portion of the stage from a second contact on the stage to the other of the slots. The conductive layer defines an open circuit when the gap is open, and the specimen closes the circuit across the gap when placed into the pair of slots.

According to still another embodiment of the present invention, a high-temperature microscale testing stage for a microscale or nanoscale specimen comprises a frame having first and second opposing ends and first and second side beams. At least one deformable force sensor beam near the first end extends laterally across the frame between the first and second side beams. A first longitudinal beam bisects said at least one force sensor beam and has a free end, and a second longitudinal beam has a free end facing the free end of the first longitudinal beam to define a gap therebetween. A support structure is disposed near the second end, and a pair of slots is disposed at each of the free ends of the first and second longitudinal beams, respectively, where each of the slots provide a seat for an end of a separately fabricated microscale or nanoscale specimen. The stage is formed of a material having a high melting temperature. In particular example embodiments, a temperature sensor is provided.

BRIEF DESCRIPTION OF THE DRAWINGS

FIG. 2A shows grooves on a longitudinal beam and a dogbone-shaped specimen, and FIG. 2B shows the dogbone-shaped specimen seated in the grooves;

FIGS. 5A-5D show SEM images of a tensile stage according to an embodiment of the present invention, where FIG. 5A shows an overall view of the stage, FIG. 5B shows a 90 μm-deep groove of a grip, FIG. 5C shows a specimen with strain measurement gauges, and FIG. 5D shows image tracking marks on the strain measurement gauges (dotted circle) and on the stage (solid circle on grip and dash-dot circle on the force sensing gauge);

FIG. 9A shows a hinge-like alignment mechanism according to an embodiment of the invention (Case I), and FIG. 9B shows a specimen without a hinge-like alignment mechanism;

FIGS. 11A-11C show experimental and analytical results for a self-aligning specimen, with gauge length of 50 μm and cross section area 90 μm², where FIG. 11A-11B shows experimental measurement of stress-strain ratio between $\in_{bottom}$ and $\in_{top}$, and FIG. 11C shows a strain ratio using an analytical model;

FIGS. 12A-12B show a specimen with I*=1.5 and I*=23, respectively, where I*=I₁/I;

FIG. 14A shows the stage without the specimen, and FIG. 14B shows the specimen mounted on the grips;

FIGS. 15A-15H show steps in an example process for fabricating the uniaxial testing stage of FIG. 13;

FIGS. 22A-22D show steps in an example fabrication method for the SiC based MEMS stage of FIG. 20;

FIG. 24B shows an enlarged portion of the SIC stage of FIG. 24A;

FIG. 26A shows an SiC stage on a piezoactuator, FIG. 26B shows heat radiation with applied electric current, and FIG. 26C shows an enlarged portion of FIG. 26B.

DETAILED DESCRIPTION

Figure 1:
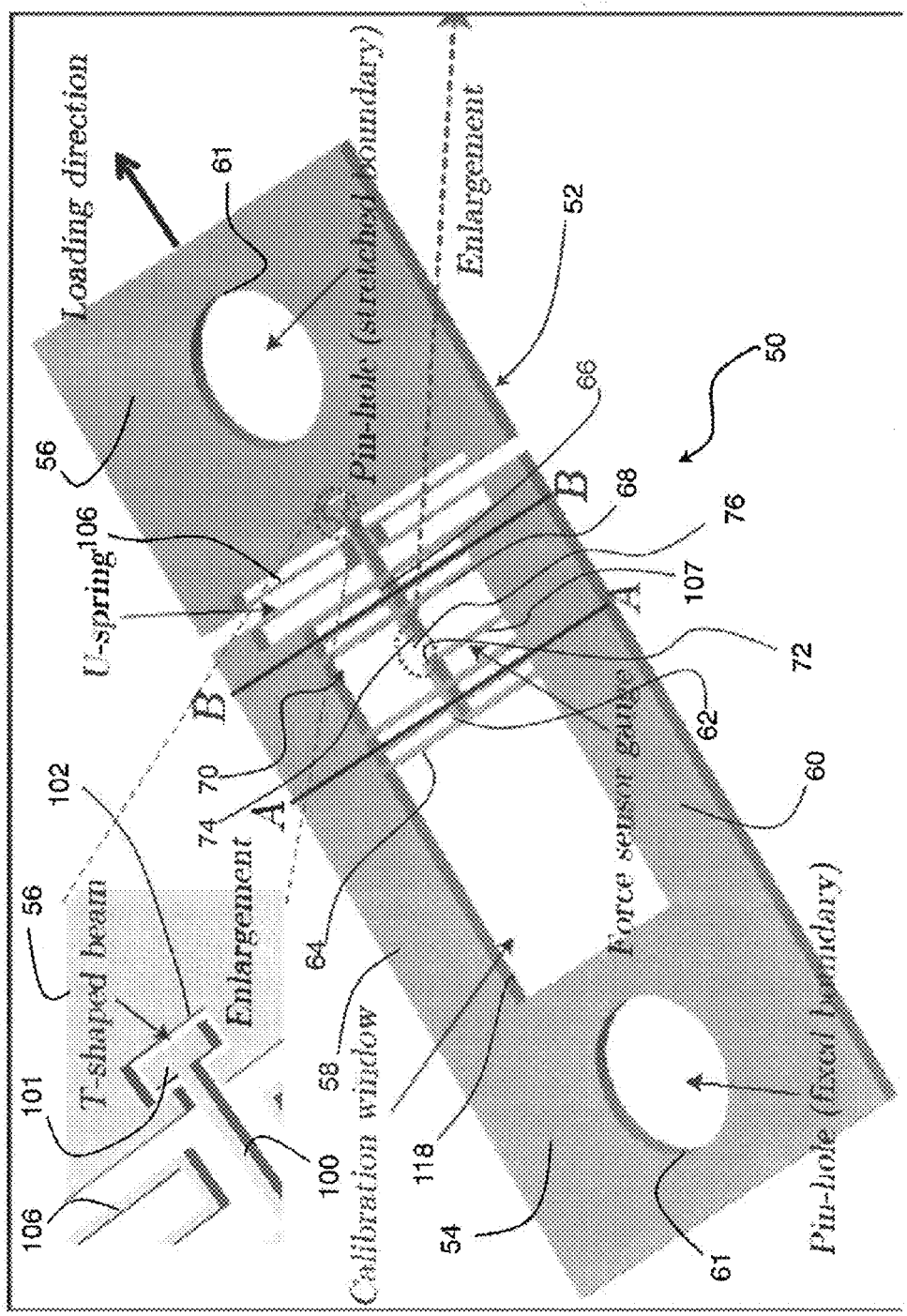
FIG. 1 shows an in situ uniaxial testing stage according to an assembly approach, including an enlarged portion showing a T-shaped beam.

Embodiments of the present invention provide, among other things, microscale testing stages and specimens for reducing misalignment during loading of a microscale or nanoscale specimen as a result of uniaxial testing. Example testing stages and specimens can be used in situ, for instance in testing environments such as (but not limited to) TEM and SEM. An example embodiment for uniaxial testing includes a testing stage and a separately fabricated microscale or nanoscale specimen. As used herein, it is to be understood that, except where indicated otherwise, descriptions related to microscale are also generally applicable to nanoscale, and vice versa.

An example testing stage includes a frame having first and second opposing ends and first and second side beams, at least one deformable force sensor beam near the first opposing end extending laterally across the frame between the first and second side beams, a first longitudinal beam bisecting the at least one force sensor beam and having a free end, and a second longitudinal beam having a free end facing the free end of the first longitudinal beam to define a gap therebetween. A support structure is disposed near the second opposing end and comprises a plurality of laterally extending beams, the second longitudinal beam bisecting the plurality of laterally extending beams. A pair of slots is disposed at each of the free ends of the first and second longitudinal beams, respectively, each of the slots providing a seat for an end of the specimen. The uniformly fabricated specimen has a longitudinally central gauge length portion and first and second hinges disposed at each of opposing longitudinal sides of the gauge length portion, which provide a self-aligning mechanism to help achieve uniaxial loading during tensile testing. Example self-aligning mechanisms resolve misaligning problems at small scale and, hence, ensure the validity of the testing results.

Embodiments of the present invention further provide, among other things, a microscale apparatus that allows mechano-electrical testing of nanoscale or microscale samples in situ. An example testing stage includes a frame having first and second opposing ends and first and second side beams, at least one deformable force sensor beam near the first opposing end extending laterally across the frame between the first and second side beams, a first longitudinal beam bisecting the at least one force sensor beam and having a free end, and a second longitudinal beam having a free end facing the free end of the first longitudinal beam to define a gap therebetween. A support structure is disposed near the second opposing end, and the support structure comprises a plurality of laterally extending beams, wherein the second longitudinal beam bisects the plurality of laterally extending beams. A pair of slots is disposed at each of the free ends of the first and second longitudinal beams, respectively, each of the slots providing a seat for an end of a separately fabricated specimen. A conductive layer or layers is provided on the testing stage to define conductive paths through at least a portion of the testing stage from each of first and second contacts on the testing stage to each of the slots, respectively. An open circuit is defined across the stage, which can be closed by the specimen when placed into the pair of slots.

The terminals may be coupled to any of various electrical devices for electrical measurement of the specimen and/or supplying current or voltage to the specimen. For example, such stages can allow concurrent measurement of mechanical and electrical properties to explore their coupled interactions. Stress-strain response, fracture strength, and piezoresistance are of great interest with MEMS and NEMS applications. An example stage is capable of measuring these properties independently and simultaneously in SEM and TEM under uniaxial loading. Example embodiments for mechano-electrical testing can also include a specimen having a self-aligning mechanism.

Other embodiments of the present invention provide an in situ uniaxial testing stage comprising a material having a high melting temperature, which allows the stage to test microscale or nanoscale samples by measuring simultaneous forces at high temperatures. An example stage is of a unitary material having a high melting temperature. The stage includes a frame having first and second opposing ends and first and second side beams, at least one deformable force sensor beam near the first opposing end extending laterally across the frame between the first and second side beams, a first longitudinal beam bisecting the at least one force sensor beam and having a free end, and a second longitudinal beam having a free end facing the free end of the first longitudinal beam to define a gap therebetween. A support structure is disposed near the second opposing end, and comprises a plurality of laterally extending beams such that the second longitudinal beam bisects the plurality of laterally extending beams. A pair of slots is disposed at each of the free ends of the first and second longitudinal beams, respectively, each of the slots providing a seat for an end of a separately fabricated specimen. Example stages can also be used for mechano-electrical measurements either through the unitary material itself or an additionally layered material, and/or for providing Joule heating through a resistive path provided by the stage. In particular example embodiments, a bi-metal temperature sensor can be provided as part of the stage for measuring the temperature of the stage.

An example MEMS or NEMS based uniaxial stage is capable of testing a wide range of material and accommodating various specimen dimensions with uniaxial tension and compression loading. Example embodiments allow testing of any of various types of materials, including organic, inorganic, or a combination of materials. Sample materials include, but are not limited to, metals (including single-crystal or polycrystal), dielectrics, biological materials, and/or multi-layer composites, that can be fabricated into a suitable shape to be used with the particular testing stage. Embodiments of the invention are particularly useful for probing microscale or nanoscale material behavior, where the deformation characteristics are expected to deviate significantly from bulk values. Because the samples are fabricated separately, a greater variety of samples are possible for material testing than that available under certain previous methods. Further, separately fabricated samples allow particular example testing stages to be reusable.

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

FIG. 1 shows an example uniaxial testing stage 50 according to an embodiment of the present invention. The testing stage 50 includes a substrate material, such as but not limited to silicon, which preferably is fabricated using microfabrication methods. The testing stage 50 includes a generally rectangular frame 52 having a first opposing end 54 and a second opposing end 56. A pair of laterally opposed side beams 58, 60 extend longitudinally between the first opposing end 54 and the second opposing end 56. The testing stage 50 may be of various dimensions. If a thin wafer (e.g., silicon) is used, a relatively small testing stage can be provided.

During testing, the first end 54 is moved relative to the second end 56, for instance using a moving stage (not shown) having pillars coupled to the testing stage 50 at apertures such as pinholes 61. For tensile testing, the first end 54 and the second end 56 are moved away from one another along a loading direction L, while for compressive testing, the first end and the second end are moved toward one another along the loading direction (the direction of the arrow L in FIG. 1 is for tensile testing). Either the first end 54 or the second end 56 may be a fixed end, while the other end is moved. Alternatively, both ends 54, 56 may be moved while loading.

For supporting a specimen (sample) to be tested, the testing stage 50 includes a first longitudinal beam 62 that is substantially laterally centered within the frame 52 and coaxial with the loading direction L. The first longitudinal beam 62 bisects one or more, and preferably several, deformable force sensor beams 64. These force sensor beams 64 extend laterally between the first and second side beams 58, 60. As shown in FIG. 1, the force sensor beams 64 extend along a lateral line such as line A-A. The force sensor beams 64 provide support to the first longitudinal beam 62, and are configured to deflect in response to a tensile or compressive stress on the sample.

Using a plurality of force sensor beams 64 in the testing stage 50 allows a larger range of spring constants when testing the sample. For example, if the sample to be used is soft, one or more of the force sensor beams 64 may be cut (such as by focused ion beam (FIB)) to lower the beam stiffness and attain higher force resolution.

The example testing stage 50 also includes a second laterally centered longitudinal beam 66, also coaxial with the loading direction L, which bisects a plurality of laterally extending beams 68. These generally rectangular beams 68, which extend laterally between the first and second side beams 58, 60 (such as along line B-B in FIG. 1), provide a support structure 70 for supporting the second longitudinal beam 56, and help to reduce misalignment during loading. While three support beams 68 are shown in FIG. 1, it will be appreciated that less than or more than three support beams are possible. Thus, the support structure 70 is not intended to be limited to the configuration shown. It is preferred, however, that a plurality of the support beams 68 be used.

As also shown in FIGS. 2A-2B, the first and second longitudinal beams 62, 66 are coaxially disposed so that free ends 72, 74 of the beams face one another, the edges of which are separated by a gap 76. These free ends 72, 74 include generally symmetrical sample slots 80, 82, which support ends of a separately fabricated sample 84 and provide sample grips. Thus, slots such as the slots 80, 82 are also referred to herein as grips. For testing, the sample 84 is placed within the testing stage 50 (such as by using a focused ion beam (FIB) omniprobe) so that first and second ends 86, 88 of the sample are seated within the sample slots 80, 82 at the free ends 72, 74. The sample 84 is partially suspended, spanning the gap 76 between the first and second longitudinal beams 62, 66 to connect the beams. A nonlimiting example length for the sample 84 is between one-half micron and twenty microns.

Figure 2:
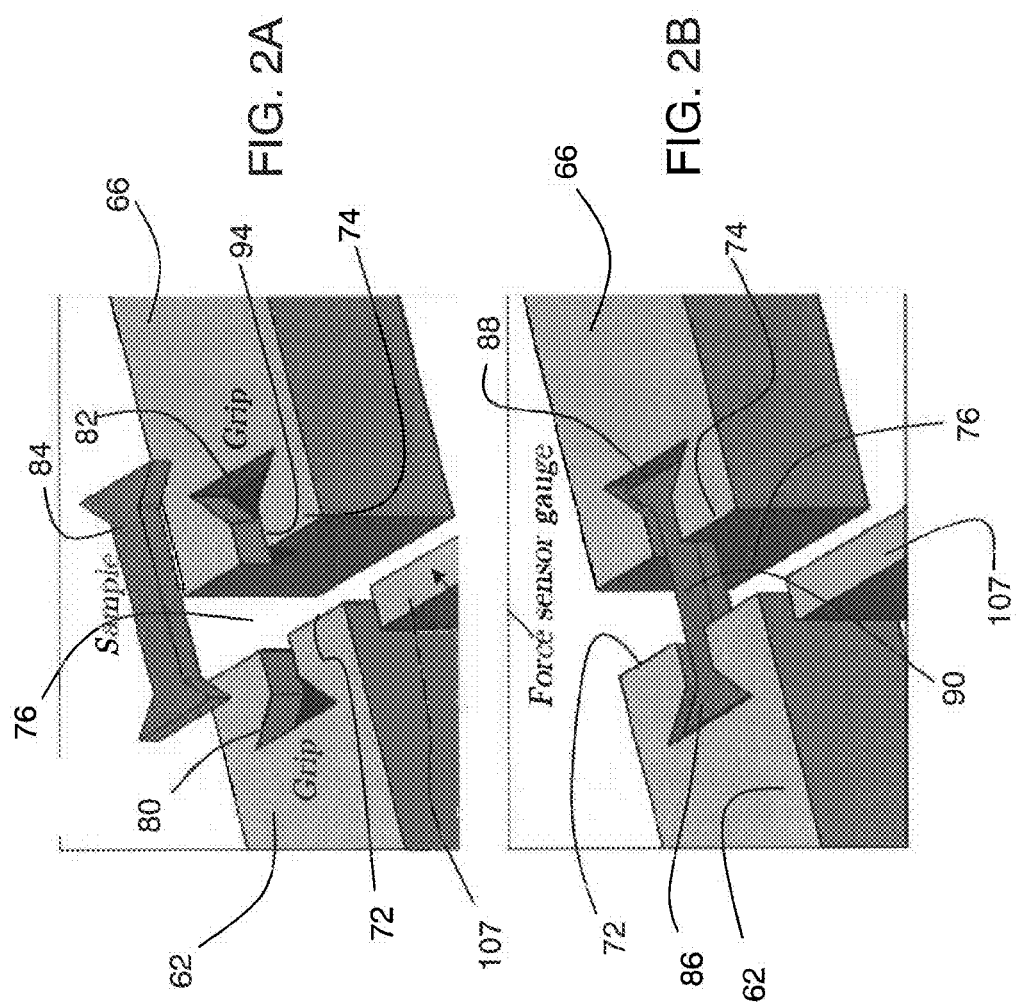
FIGS. 2A-2B show an enlarged portion of the uniaxial testing stage of FIG. 1, where

The sample 84 shown in FIG. 2 is formed into a dogbone shape, and the sample slots 80, 84 in the free ends 72, 74 can be similarly patterned in complementary parts to receive the sample. Other example shapes for the slots 80, 84 are shown and described in U.S. patent application Ser. No. 11/897,927, filed Aug. 31, 2007. The sample 84 generally includes a pair of enlarged, longitudinally opposed ends 86, 88 having at least a portion tapered inwardly to a more narrow longitudinal portion 90 extending therebetween. Similarly, the sample slots 80, 82 may each include a laterally enlarged portion 92 that tapers inwardly to a narrower, longitudinal portion 94. The longitudinal portions 94 of the sample slots 80, 82 are coaxial with the loading direction. The sample slots 80, 82 can be formed by patterning and Si etching, FIB, and/or other methods. A nonlimiting example material for the sample 84 is single crystal silicon, with a crystal orientation <110>.

The support structure 70 supporting the second longitudinal beam 66 transmits the displacement between the first and second ends 54, 56 of the testing stage 50 to the sample 84 during testing via the second longitudinal beam. The support beams 68 also correct load misalignment between the loading direction and the load axis of the load axis of the sample 84. Similarly, the force sensor beams 64 indicate a force transmitted to the sample 84 via the first longitudinal beam 62. Both the support beams 68 and the force sensor beams 64 preferably are compliant in the in-plane transverse direction, but stiff in other directions, due to high depth to width ratio (e.g., 150/10~150/60).

For preventing premature loading of the sample 84 within the testing stage 50, the second longitudinal beam 66 preferably terminates beyond the support structure 70 in a cantilevered support end 100 opposite the free end 74. The support end 100 extends laterally from the center of the second longitudinal beam 66, forming a symmetrical, generally T-shaped end 101. An opening 102 is formed in the second end 56 to accommodate the support end 100, and this opening is slightly larger than the T-shaped support end 101 to provide a pair of small gaps on longitudinally opposed sides of the cantilevered end. During testing, tensile loading and compressive loading, the testing stage 50 has to be pulled or pushed, respectively, to close one of the gaps before imparting a load on the sample 84.

To further correct misalignment between the sample 84 and the loading direction, and for providing additional structural integrity to the testing stage 50, a pair of springs 106 such as U-shaped springs is provided at each lateral side (respectively) near the side beams 58, 60 or elsewhere on the testing stage. These springs 106 deform when the first end 54 and the second end 56 are pulled apart during relative movement (e.g., during actuation of the testing stage 50), and thus substantially prevent the side beams 58, 60 between the springs and the first end 54 from deforming. This also facilitates transmission of the displacement between the ends 54, 56 along the second longitudinal beam 66 to the sample 84. Cutouts (not shown) may be provided within the side beams 58, 60 for providing additional structural integrity.

The inward edges at the facing front ends 72, 74 of the first and second longitudinal beams 64, 66 can provide displacement gauges for measuring stress of the force sensor beams 64 and displacement of the ends 86, 88 of the sample 84. As shown in FIGS. 1-2, a center gauge 107 is provided by a beam that extends laterally from the side beam 60 toward the edges, functioning as a reference. Cutouts (not shown) at the inward edges may be provided to further define the displacement gauges (e.g., to provide a larger range of measurement without interfering with the sample 84).

It will be appreciated that additional or alternative displacement gauges or markers may be provided on the testing stage 50 or the sample 84 at different locations to measure the displacement in the sample and the force on the sample. Locating displacement gauges or markers near the sample 84, though, allows the gauges or markers to be read simultaneously with observation of the sample. This may be especially useful during in situ monitoring and testing, such as within a TEM or SEM chamber, to enable simultaneous study of the sample's quantitative response as well as its microstructural and topological evolution during deformation.

Figure 3:
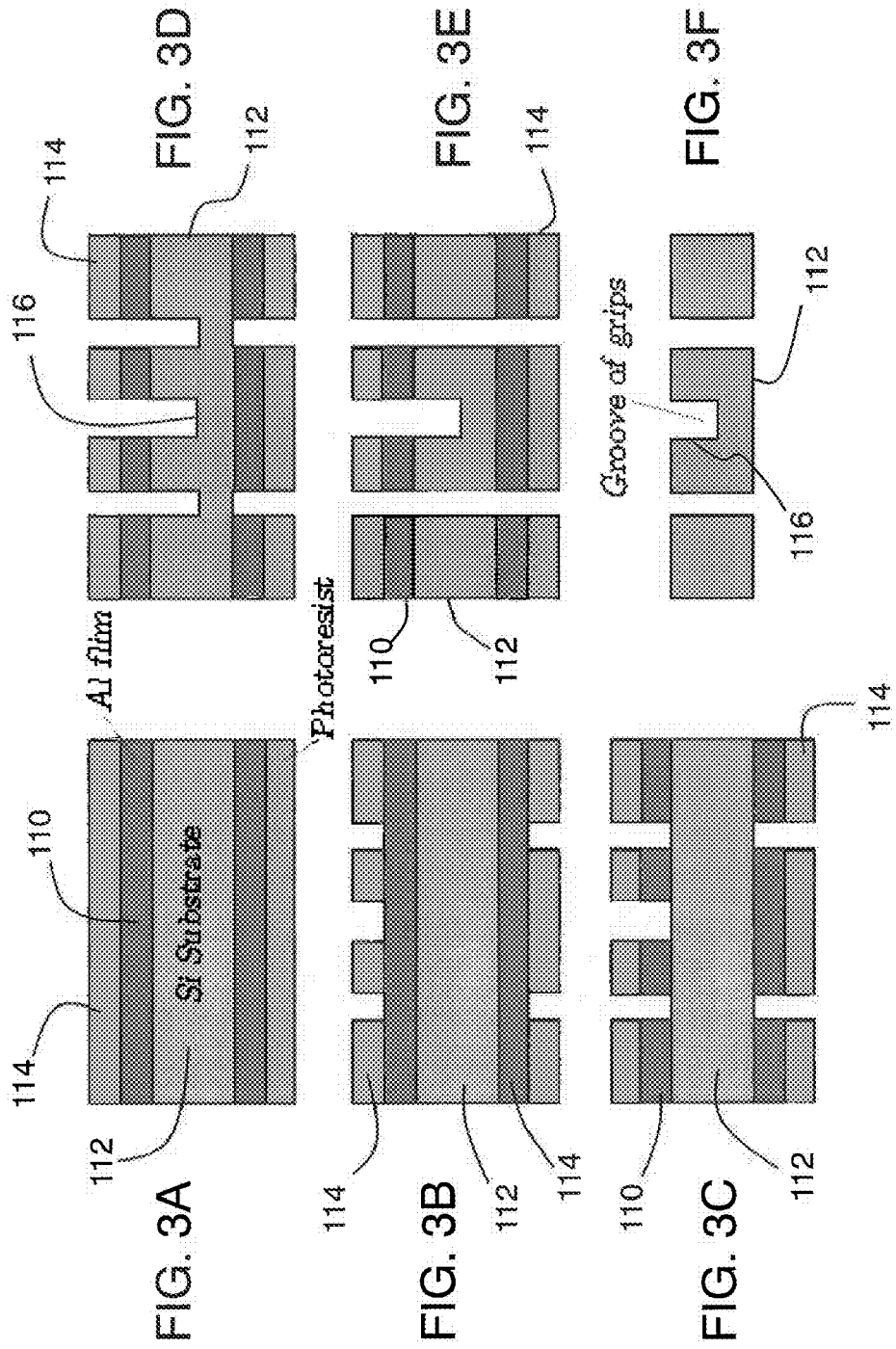
FIGS. 3A-3F show respective steps in a fabrication process for the testing stage of FIG. 1.

FIGS. 3A-3F show an example process for fabricating the testing stage 50. As shown in FIG. 3A, Al films 110 are deposited on both sides of a silicon wafer 112, followed by a layer 114 formed by photoresist (PR) spin-coating. Then, the photoresist layer 114 and the Al film layers 110 are patterned by lithography (FIG. 3B) and wet etching (FIG. 3C). The patterned Al layers 110 serve as masks during an inductively coupled plasma-deep reactive ion etching (ICP-DRIE) process. The silicon wafer 112 is etched from the top to make grooves 116 for grips 80, 82 (FIG. 3D) and then from the bottom to release free-standing structures (FIG. 3E). After etching, the photoresist layers 114 and the Al masks 110 are removed (FIG. 3F).

Upon loading, the support springs 68 transfer the deformation to the specimen 84. In an example testing stage 50, the U-beams 106 suppress misalignment between the pillar and the grips 82, 84 by six orders of magnitude (e.g., 18° loading alignment error can be reduced to $1.33 \times 10^{-5}$ degrees misalignment at the grips). The specimen 84 and the force sensor beams 64 are in series. Therefore, the load in the specimen 84 is obtained from the deformation of the beams 64, where the stiffness of the beams is calibrated by a scale. A desired high resolution of the force sensor beams 64 can also be achieved by decreasing the width of the force sensor beams. In an example operation, after the calibration of the force sensor beams 64, the tensile stage 50 and the specimens are assembled, for instance, in an FIB (e.g., an FEI Dual Beam 235 FIB) chamber for assembly using the FIB omniprobe. The specimen may be fixed to the probe (e.g., by Pt deposition), and after assembly the specimen may be released from the probe (e.g., by FIB milling).

To apply load on the sample 84, the testing stage 50 is actuated so that the appropriate gap at the opening 102 becomes closed for tensile or compressive testing. Further actuation applies load on the sample 84, and the displacement gauges and/or markers are moved relative to one another to provide deflection of the force sensor beams 64, which can be used to calculate the force on the sample 84 by multiplying with the stiffness of the force sensor beams. The relative movement of the displacement gauges and/or markers also provides the deformation and thus the strain of the sample 84. The strain response of the specimen is correlated with the applied stress.

In a particular nonlimiting example operation for tensile testing, scanning electron microscope (SEM) images are taken to measure strain and stress of the specimen 84 simultaneously. A correlation algorithm is used to track arbitrary marks automatically with resolution enhancement up to 1/10 of pixel size. Image tracking marks in an example embodiment are created on the stage 50 and the specimen 84 by FIB milling. The marks on the stage 50 may be located, for instance, on one or both of the grips 80, 82 and on the force sensing gauge 107. For the specimen 84, several marks can be created along the vertical surface, for instance near top, bottom, and neutral planes of the specimen. These marks allow for independent measurement of the strain corresponding to the different planes away from the neutral plane, and the systematic investigation of non-uniform loading during the test. Again, though tensile testing is described in this example, stages such as the testing stage 50 are preferably capable of both tension and compression tests.

In an example method for calibrating the force sensor beams 64, the effect of geometric nonlinearity of the force sensor beams is considered. This effect is due to the beam's 64 transverse deformation $\delta$ along the loading direction L. The force sensor beams 64 are anchored to the frame 50 at their ends, and therefore the beams not only bend, but also stretch during large deformation. Thus, a force-displacement relation becomes $$f = \bar{k}\delta + \bar{k}_3 \delta^3$$

where $\bar{k}$ is a linear spring constant, and $\bar{k}_3$ is a nonlinear spring constant. The linear and nonlinear spring constants of N pairs of the force sensor beams 64 (e.g., at A-A in FIG. 1) can be written as $$\bar{k} = 16N \left( \frac{E_{SB} b_{SB}^3 h_{SB}}{l_{SB}^3} \right) \text{ and } \bar{k}_3 = 8N \left( \frac{E_{SB} b_{SB} h_{SB}}{l_{SB}^3} \right),$$

where $E_{SB}$, $b_{SB}$, $h_{SB}$, and $l_{SB}$ are Young's modulus, width, depth, and length of the force sensor beams 64, respectively. Values of $\bar{k}$ and $\bar{k}_3$ can be calibrated experimentally by applying a known force on the beam and measuring its deflection. A weighing scale can be used to measure the force, and an optical microscope can be used to measure the displacement $\delta$ of the force sensor beams 64.

Figure 4:
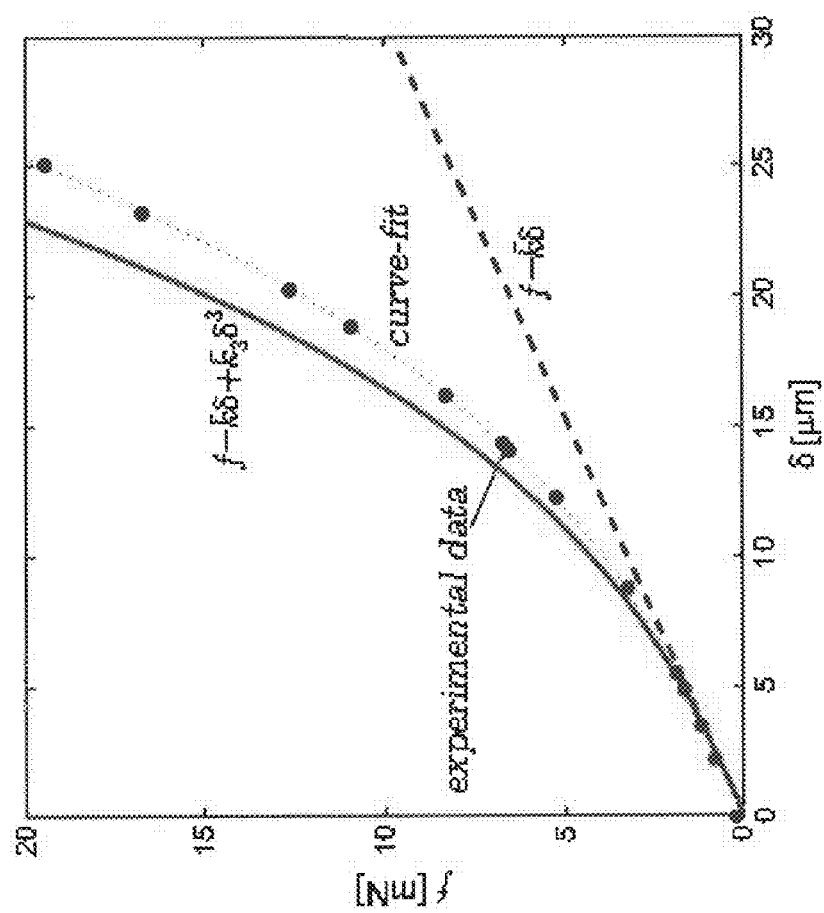
FIG. 4 shows a force-displacement curve from calibration of force-sensing values, where solid circles show experimentally measured force-displacement response, where the experimental data is fitted by $f=\bar{k}\delta+\bar{k}_3\delta^3$ and linear and non-linear spring constants are obtained, and where spring stiffness of force sensing beams are predicted by a linear ($\bar{k}\delta$) and nonlinear ($\bar{k}\delta+\bar{k}_3\delta^3$) approximation (with $\bar{k}$ and $\bar{k}_3$ predicted from geometry and elastic property of single crystal silicon)

FIG. 4 compares experimentally obtained calibration data with analytical results with and without the nonlinear spring term, and a best fit curve with $\bar{k}=0.322$ mN/μm, and $\bar{k}_3=7.259 \times 10^{-4}$ mN/μm$^3$. These values are close to the predicted values of $\bar{k}=0.325$ mN/μm and $\bar{k}_3=10.426 \times 10^{-4}$ mN/μm$^3$. The predicted values were slightly higher due to overestimation of the size of the beams, as the geometry of the force sensing beams was evaluated from SEM images, which induces a calibration error. Alternately, a separately fabricated calibrator may be inserted into a calibration window 118, as described in U.S. patent application Ser. No. 11/897,927 to Han et al.

As stated above, alignment is a significant consideration for accuracy of uniaxial testing stages. For example, misalignment between the axis of loading and the sample axis results in non-uniform stress on the cross-section of the sample as well as along its gauge length. The degree of misalignment may change in a given experiment with increasing load due to the shift of the location of the load at the grip. This shift is due to compliance of the sample and/or the loading stage, resulting in a nonlinear relation between the measured applied load and strain at a point on the surface of the sample, even though the strains are small and the materials are linear elastic.

In the case of ideal alignment, the neutral axes of the grips 80, 82 are precisely aligned with a neutral axis of the testing frame 50. Moreover, these aligned components are in line with the specimen 84 neutral axis, such as along a centerline of the longitudinal portion 90. Misalignment in uniaxial tests in general is caused by a combination of poor alignment of grips (transverse misalignment (TM)), poor conformance of specimen and grips (rotational misalignment (RM)), and inaccurate machining of the test specimen itself (misalignment due to shape of tested materials (MS)). A combination of these three sources of misalignment, which occur simultaneously, operates in uniaxial tests. The main influence of this combined misalignment is stress and strain gradients across a specimen, where the extreme stresses and strains occur at the surfaces. Validity of testing results can be affected by these gradients.

It is particularly difficult to achieve uniaxial loading in small scale. Unlike macroscale uniaxial testing instruments, it can be challenging to utilize alignment devices, achieve precise alignment between grips and a specimen, and fabricate an exact specimen shape for microscale or nanoscale testing due to the small size that is required.

In the example testing stage 50, RM can be made very small due to the provided U-shaped springs 106, in combination with an accurate alignment between the grips 80, 82. To help minimize TM, a tensile stage 120 is shown in FIGS. 5A-5D according to another embodiment of the present invention. The testing stage 120 is generally similar to the testing stage 50 shown in FIG. 1, and like parts are indicated with like reference characters. However, to reduce TM, grips 122, 124 are provided that have a depth to about mid-height of the stage 120 (which depth may also be adjusted to accommodate the thickness of the sample), as shown in FIG. 5B. This suppresses the effect of the compliance of the stage 120, as otherwise asymmetry of the sample location with respect to mid-height of the stage 120 results in bending of the stage. In the example testing stage 120 having a stage height of 150 μm and a sample thickness of about 30 μm, the example grips 122, 124 have a depth of 90 μm (15 μm deeper than 75 μm to compensate for the sample thickness).

To enhance the resolution of the force measurement, force sensing beams 126 are provided having a reduced beam width, as shown in FIG. 5A. In the example testing stage 120, the width of the force beams is reduced from 60 μm to 12 μm, and accordingly the resolution of the force measurement is enhanced by two orders of magnitude. These (thinner) force sensing beams 126 lead to large transverse deformation, and thus the nonlinear spring constant $\bar{k}_3$ is properly considered.

Also, as shown in FIGS. 5C-5D, a specimen 130 is provided having the general dogbone shape of the specimen 84, but further includes freestanding arms 132, 134 having a portion extending parallel to a gauge length 135 that provide a strain measurement gauge for strain resolution enhancement. As best seen in FIG. 5D, the arms 132, 134 include top and bottom image tracking marks 136, which in combination with tracking marks 138 formed on the stage and tracking marks 140 formed on the center gauge 107 provide automated stress-strain measurement with resolution enhancement. The strain measurement gauge 132, 134 ensures that the gauge length 135 of the specimen is free from any influence of FIB ion milling, or an electron beam, e.g., in the SEM.

Figure 6B:
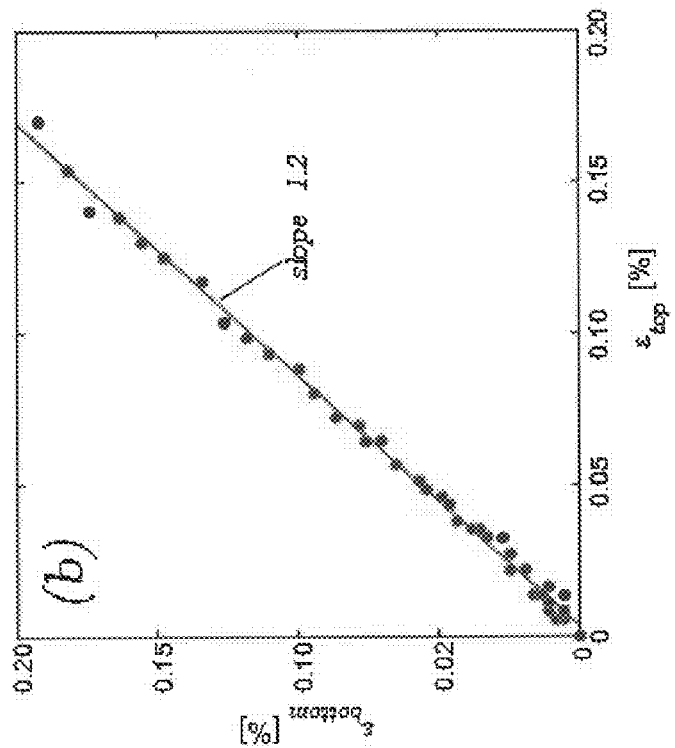
FIGS. 6A-6B show experimental and analytical results for a 540 μm-long specimen with cross-section area A=77 μm², showing shows stress-strain response and strain ratio between $\in_{bottom}$ and $\in_{top}$.
Figure 6A:
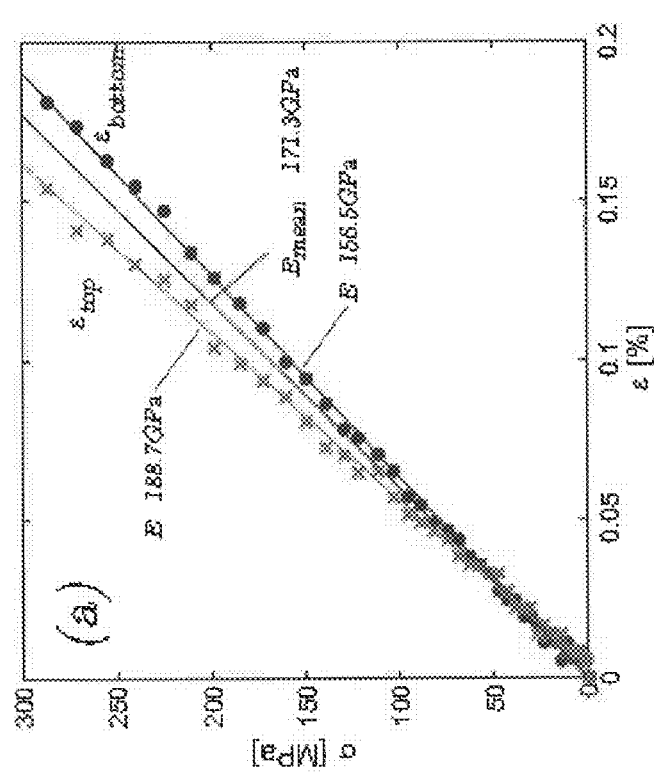

FIGS. 6A-6B show stress-strain curves and $\in_{bottom}$ versus $\in_{top}$ curves for a 540 μm specimen with cross sectional area A=77 μm². The apparent moduli of the specimen are $E_{top}$=189 GPa and $E_{bottom}$=157 GPa. $E_{mean}$=σ/$\in_{ave}$ is 171 GPa with 1.2% relative error with respect to $E_{exa}$. The slope of the $\in_{bottom}$-$\in_{top}$ curve is 1.2 by linear fit.

To further minimize non-uniform loading from grips, a specimen is provided according to additional embodiments of the present invention that includes a self-aligning mechanism between grips and the gauge length of the specimen. The self-aligning mechanism prevents bending from being transferred to the specimen, thus providing a reliable method to test mechanical properties of microscale and nanoscale specimens with uniaxial loading. Finite element analysis shows a significant reduction of the non-uniform stress in example specimens. Tensile testing of example single crystal silicon specimens gives an expected elastic modulus.

Figure 7:
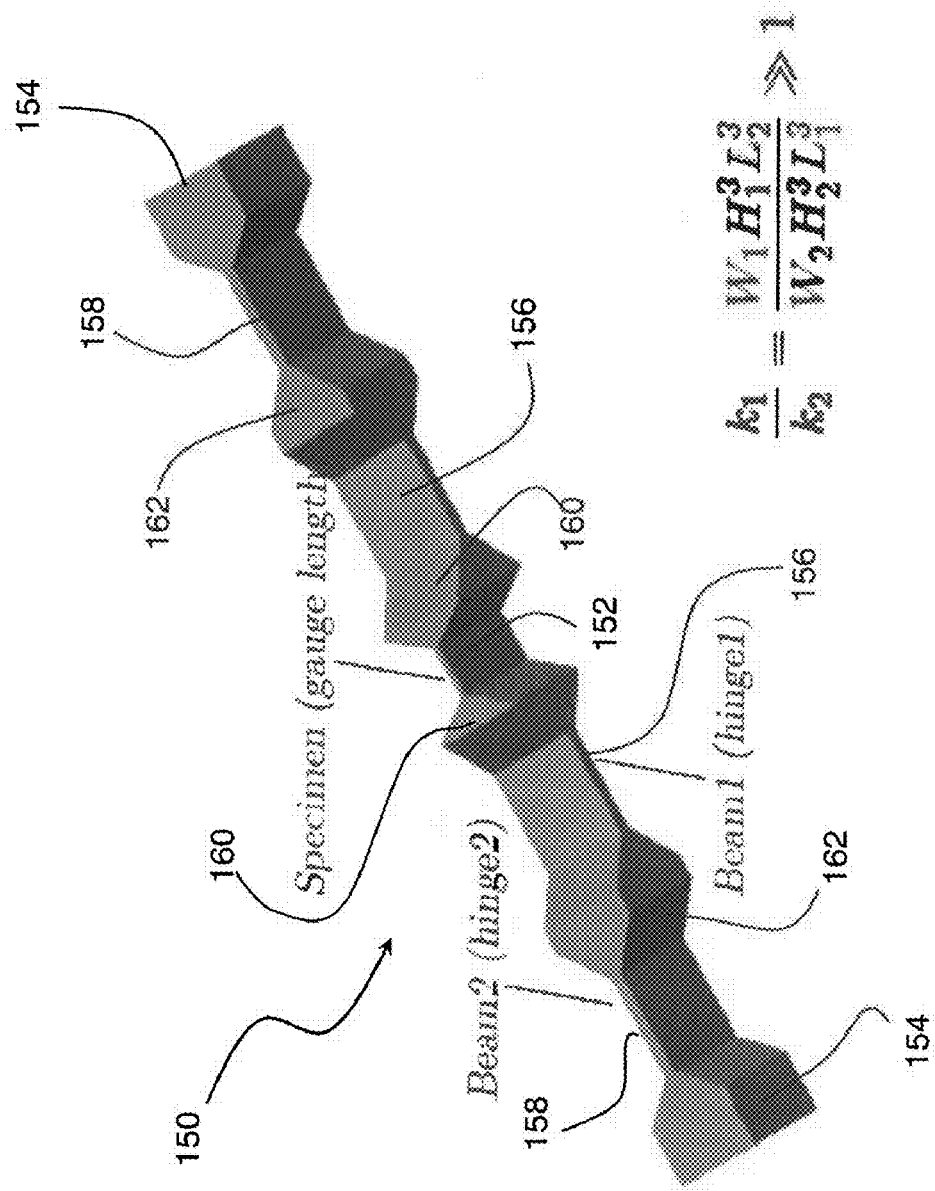
FIG. 7 shows a self-aligning specimen, according to an embodiment of the present invention.
Figures 8A, 8B:
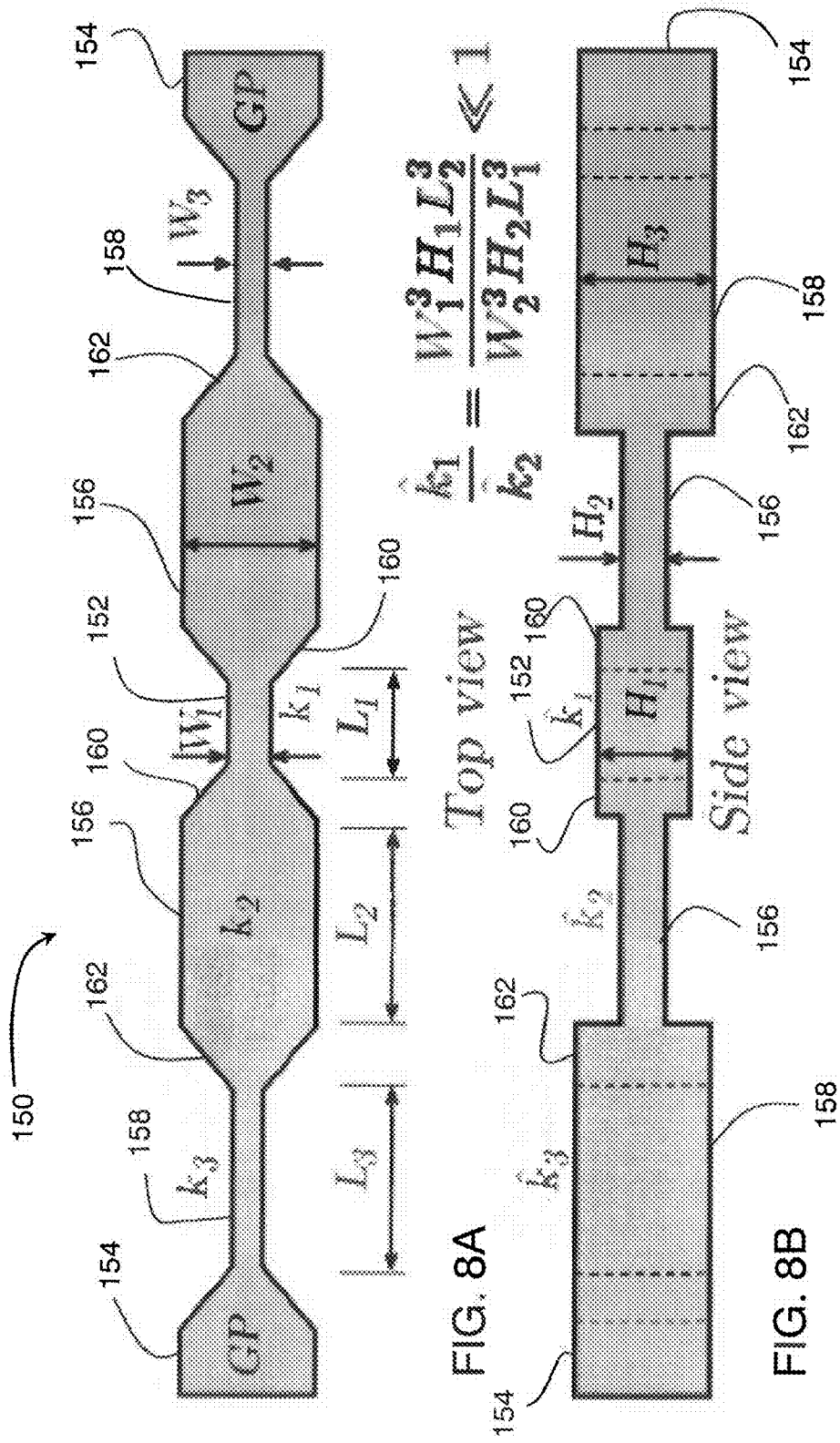
FIGS. 8A and 8B show a top view and side view, respectively, of the self-aligning specimen of FIG. 7.

FIGS. 7 and 8A-8B show a specimen 150 according to an example embodiment. The preferably unitary material specimen 150 includes a centrally disposed gauge length portion 152 and outer portions 154 providing gripped parts. The outer portions 154 may be made similarly to the samples 84, 130, or may have other configurations. To provide a self-aligning mechanism, a pair of self-aligning beams 156, 158 is provided on both longitudinally opposed sides of the gauge length portion 154. An inner pair of self-aligning beams 156 is disposed respectively between the gauge length portion 152 and the outer portions 154 at either end, separated from the gauge length portion by a transition portion 160. An outer pair of self-aligning beams 158 is disposed between the inner self-aligning beams 156 and the outer portions 154, separated from the inner self-aligning beams by a transition portion 162. Each of the aligning beams 156, 158 are flexible in designed bending directions such that they behave as hinges connected to the gauge length portion 154. This leads to significant reduction in bending and improves validity of testing results.

In the example specimen 150, cross-sectional areas of the aligning beams 156, 158 are larger than that of the tested part (the gauge length portion 152) so that the mean stress in the self-aligning beams is always smaller than that in the gauge length portion. Additionally, the bending stiffness of the self-aligning beams 156, 158 is much smaller than that of the gauge length portion 152, so that any bending due to misalignment from grips can be suppressed by the self-aligning beams.

These example features will now be described more particularly with respect to FIGS. 8A-8B. The specimen 150 generally includes the gripped parts (GP) 154, the gauge length portion of the specimen 152, inner self-aligning beams 156, each of which are referred to in the equations that follow as self-aligning beam I, and outer self-aligning beams 158, each of which are referred to as self-aligning beam II, separated by transition portions 160, 162. Note that despite the use of "I" and "II," the locations of the beams 156, 158 and their respective directions can be reversed in other embodiments. The dimensions of respective parts can be defined by $W_i$, $H_i$ and $L_i$, where i=1, 2, and 3 correspond to the gauge length portion 152, self-aligning beam I 156, and self-aligning beam II 158, respectively. The difference in cross-sectional areas described above indicates that $W_1H_1<W_2H_2$ and $W_1H_1<W_3H_3$. This ensures that the mean stress in each of the self-aligning beams 156, 158 is always smaller than that in the gauge length portion 152.

The other general feature described above is that the bending stiffness of the self-aligning beams 156, 158 is much smaller than that of the gauge length portion 152 about a designed direction. For instance, self-aligning beam I and self-aligning beam II preferably are configured to be compliant in an out-of-plane bending direction and an in-plane bending direction, respectively (though, again, these directions can be reversed). Hence, the bending stiffness ratios between the specimen gauge length 152 and the self-aligning beam I 156 are $$\frac{k_1}{k_2} = \frac{W_1 H_1^3 (2L_2)^3}{W_2 H_2^3 L_1^3} \gg 1 \text{ and } \frac{\tilde{k}_1}{\tilde{k}_2} = \frac{W_1^3 H_1 (2L_2)^3}{W_2^3 H_2 L_1^3} \ll 1$$

for out-of-plane and in-plane bending directions, respectively. Likewise, the bending stiffness ratios of the specimen gauge length 152 to the self-aligning beam II 158, are ($k_1/k_2 \gg 1$ and $\tilde{k}_1/\tilde{k}_3 \gg 1$). Accordingly, the cross-sectional area of self-aligning beams 156, 158 is larger than that of the specimen gauge length 152, but the beams are designed to behave as hinges with a large bending stiffness ratio.

Figure 9A:
FIGS. 9A and 9B show cases for analyzing misalignment, where
Figure 9B:

To predict the response of the self-aligning specimen 150 analytically upon loading, the system is simplified by one dimensional beams due to the high ratio of length to height (e.g., >50). FIG. 9A shows a schematic for a first case (Case I) with a hinge-like self-aligning mechanism according to an embodiment of the present invention. FIG. 9B shows a schematic for a second case (Case II) without a hinge-like mechanism. $L_i^*$ and $I_i^*$ are length and moment of inertia, respectively. The beams shown have pinned-pinned boundary conditions.

The governing equation of such beams which are subjected to bending, M, is $$M = -EI \frac{d^2 y}{dx^2}.$$

The governing equation can be solved for Case I $$-EI_i^* y = \frac{M}{2} x^2 + d_i x + e_i$$

where $d_i$ and $e_i$ are coefficients with i=1, 2, and 3. They can be obtained using boundary conditions $$\begin{cases} y_1(x=0) = 0 \\ y_1(x=L_1^*) = y_2(x=L_1^*) \\ \frac{dy_1}{dx}(x=L_1^*) = \frac{dy_2}{dx}(x=L_1^*) \\ y_2(x=L_1^*+L_2^*) = y_3(x=L_1^*+L_2^*) \\ \frac{dy_2}{dx}(x=L_1^*+L_2^*) = \frac{dy_3}{dx}(x=L_1^*+L_2^*) \\ y_3(x=2L_1^*+L_2^*) = 0 \end{cases}.$$

The governing equation for Case I and the boundary conditions give $$\begin{cases} d_1 = \dfrac{-M(2I_2^*L_1^* + I_1^*L_2^*)}{2I_2^*} \\ d_2 = -\dfrac{M(2L_1^* + L_2^*)}{2} \\ d_3 = \dfrac{M(I_2^*L_2^* + 2I_2^*(L_1^* + L_2^*))}{2I_2^*} \\ e_1 = 0 \\ e_2 = \dfrac{M(I_1^* - I_2^*)L_1^*{}^2}{2I_1} \\ e_3 = -\dfrac{ML_2(I_1^* - I_2^*)(2L_1^* + L_2^*)}{2I_2^*} \end{cases}.$$

Likewise, the governing equation and the boundary conditions, $y(x=0)=0$ and $y(x=2L_1+L_2)=0$, lead to $$\begin{cases} d = \dfrac{M(2L_1^* + L_2^*)}{2} \\ e = 0 \end{cases}$$

for Case II. Let the undercut angle be $\theta_{Grip}$. Then, the critical bending moments, $M_{c1}$ and $M_{c2}$, which correspond to the $\theta_{Grip}$ for the Case I and II are $$\theta_{Grip} = \frac{M_{C1}(2L_1^*I_1^* + L_2^*I_1^*)}{2EI_1^*I_2^*} \text{ and } \frac{M_{C1}(2L_1^* + L_2^*)}{2EI_2^*},$$

respectively. Finally, the critical bending moment ratio, $\gamma$, can be written as $$\gamma = \frac{M_{C1}}{M_{C2}} = \frac{2\eta\kappa + \eta}{\eta + 2\kappa}$$

where $\eta = I_1^*/I_2^*$ and $\kappa = L_1^*/L_2^*$. When $\gamma \ll 1$, the moment which leads to full engagement of grip can be reduced significantly.

Figures 10A, 10B:
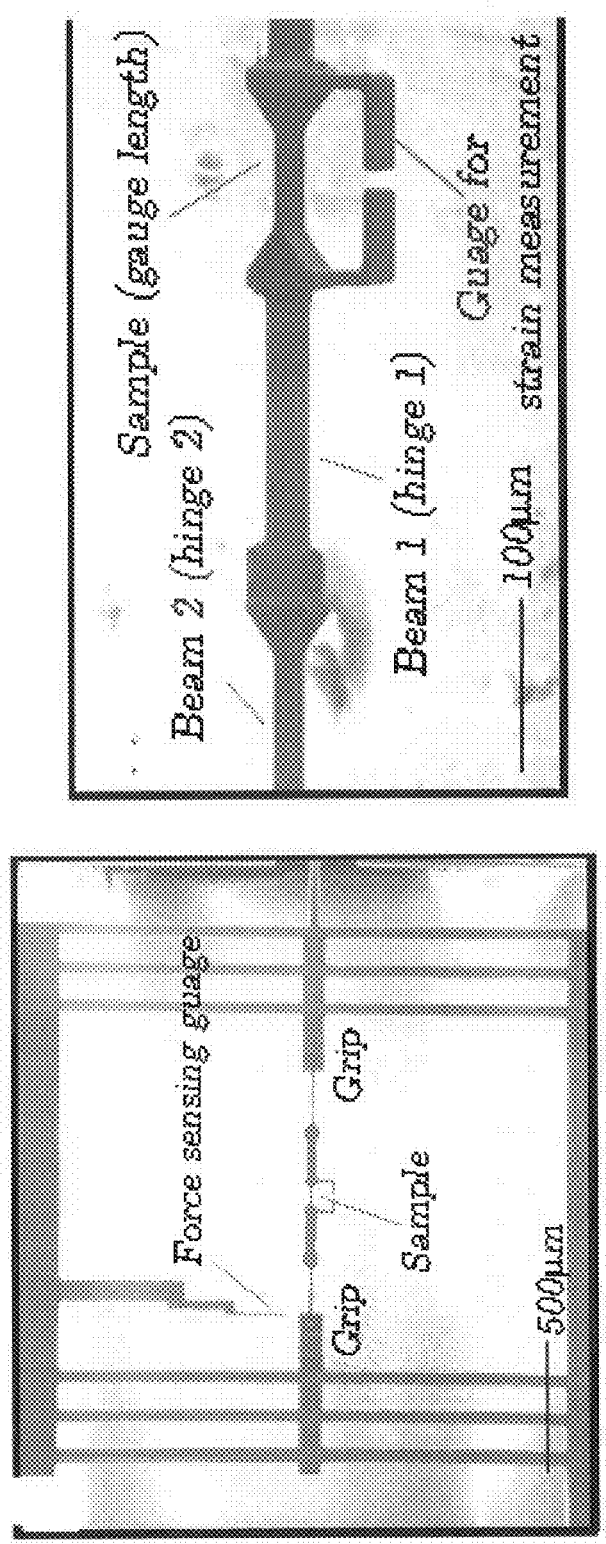
FIGS. 10A-10B show an SEM image of the self-aligning specimen of FIG. 7 loaded onto the tensile stage of FIGS. 5A-5D, with FIG. 10B showing an enlarged portion of the specimen in FIG. 10A.

Example self-aligning specimens 150 are fabricated by microfabrication and FIB milling. An example fabricated sample is shown in FIGS. 10A-10B. The inner and outer self-aligning beams 156, 158 are modified by FIB milling, during which the gauge length (tested material) 152 is preferably never directly exposed to ion beam. Measurement arms are provided on the specimen 150, including a portion extending parallel to the gauge length 152. The example measurement arms are supported by the transition portion 160.

An example gauge length portion 152 is 50 μm long with A=5 μm×18μ, and a self-aligning sample is used with $I^* = I_{gauge}/I_{hinge} = 1.5$, shown in FIG. 11B, where $I_{hinge}$ and $I_{gauge}$ are moment of inertia for the beam 1 (hinge 1) and the gauge length portion (see FIG. 10B). The length of beam 1 is about 160 μm. The stress-strain relation and $\in_{bottom}$ versus $\in_{top}$ curve are shown in FIGS. 11A and 11B, respectively. The apparent elastic moduli of the specimen are $E_{top}=180$ GPa and $E_{bottom}=160$ GPa. $E_{mean}$ is 170 GPa, with 0.6% relative error with respect to $E_{exa}$. The strain ratio, $\in_{bottom}/\in_{top}=1.1$, is obtained by linear fit. Error in the measured elastic modulus on the top of the sample is $e_m=6.1\%$, and at the bottom of the sample is 5.6%. The difference in the magnitude of $e_m$ at the top and at the bottom of the sample is further reduced.

Next, the same sample is used but with increased $I^*(I_{gauge}/I_{hinge}=23)$. The $\in_{bottom}-\in_{top}$ curve is shown in FIG. 11B. As expected, the stress uniformity in the sample is further improved for large $I^*$ since $\in_{bottom}/\in_{top}=1.02$.

FIG. 11C shows an analytical prediction of the $\in_{bottom}-\in_{top}$ curve for $I^*=1.5$ and 23 with load f at the top of the sample (the maximum possible gripping misalignment). FIGS. 12A-12B show example specimens having $I^*=1.5$ and 23, respectively. For $I^*=1.5$, $\in_{bottom}/\in_{top}=1.06$, while, $\in_{bottom}/\in_{top}\approx 1$ (even close to $\in\sim 0$) for $I^*=23$. The transition in $\in_{bottom}/E_{top}$ from negative to positive occurs at $\in_{top}<0.05\%$ for both the cases shown in FIG. 11C. Experimentally, the transition from negative to positive slopes for $I^*=23$ occurs at much smaller values of strain that is not detectable, since the misalignment at the grip was less than that considered in example analysis. Further reduction in bending can be achieved by varying design parameters of self-aligning beams such that the critical bending moment ratio, γ, can be minimized.

Thus, specimens 150 according to example embodiments having self-aligning hinges can significantly reduce non-uniform stress. By providing multiple hinges such as hinges 160, 162, the influence of unaccounted misalignment errors is eliminated or minimized even when the misalignments at the grips 80, 82, 122, 124 induce in- and out-of-plane bending. Thus, the example hinges 160, 162 allow almost ideal uniaxial loading for microscale or nanoscale uniaxial tests. Accordingly, even when single strain measurement either at the top or bottom of the sample is available, the elastic modulus can be measured accurately.

Application of strain to a crystal leads to a change in electrical conductivity due to the piezoresistance effect. Piezoresistance effect has been extensively studied and used for mechanical sensors with high sensitivity and good linearity. More recently, the drive for miniaturization of such sensors has resulted in increased attention to the material properties at macro/nano scale. Due to the size dependence of material properties, their bulk properties cannot be extrapolated to small scale directly. Further, observed superplasticity of well-known brittle materials, for instance, suggests that large strain should be imposed to small samples for complete mechano-electrical characterization.

Hence, independent and simultaneous in situ measurement of resistance for a small scale sample along with stress-strain response is essential for characterization of mechano-electrical properties and deformation mechanism of materials. However, characterization of mechano-electrical properties for small volume samples involves several challenges, including sample preparation and manipulation, measuring force and displacement with high resolution, and electrical connection to the sample and reliable resistance measurement. Thus, MEMS based apparatuses and methods are provided, which allow concurrent in situ measurement of mechanical and electrical properties to explore their coupled interactions up to sample fracture strength.

According to another embodiment of the present invention, a micro-apparatus (e.g., MEMS-based apparatus) is provided that allows mechano-electrical testing of nanoscale or microscale samples in situ, e.g., in SEM and TEM. In example tests using such an apparatus, in situ observation of samples at high resolution can reveal fundamental mechanism of deformation of materials and their size dependence at small scale. Example embodiments of the present invention allow concurrent measurement of mechanical and electrical properties to explore their coupled interactions. The sample (specimen) to be tested can be fabricated separately from the testing stage. Hence, samples from a wide range of materials and sizes can be tested. Example testing stages may be employed, for instance, to measure stress-strain response, fracture strength, and/or electrical resistivity as a function of strain of single crystal silicon (or other materials) with sample dimensions from $10^2$ down to $10^{-1}$ μm$^2$. The known elastic modulus can be recovered, as well as piezoresistive properties of SCS, with high (e.g., 99.99%) accuracy.

Figure 13:
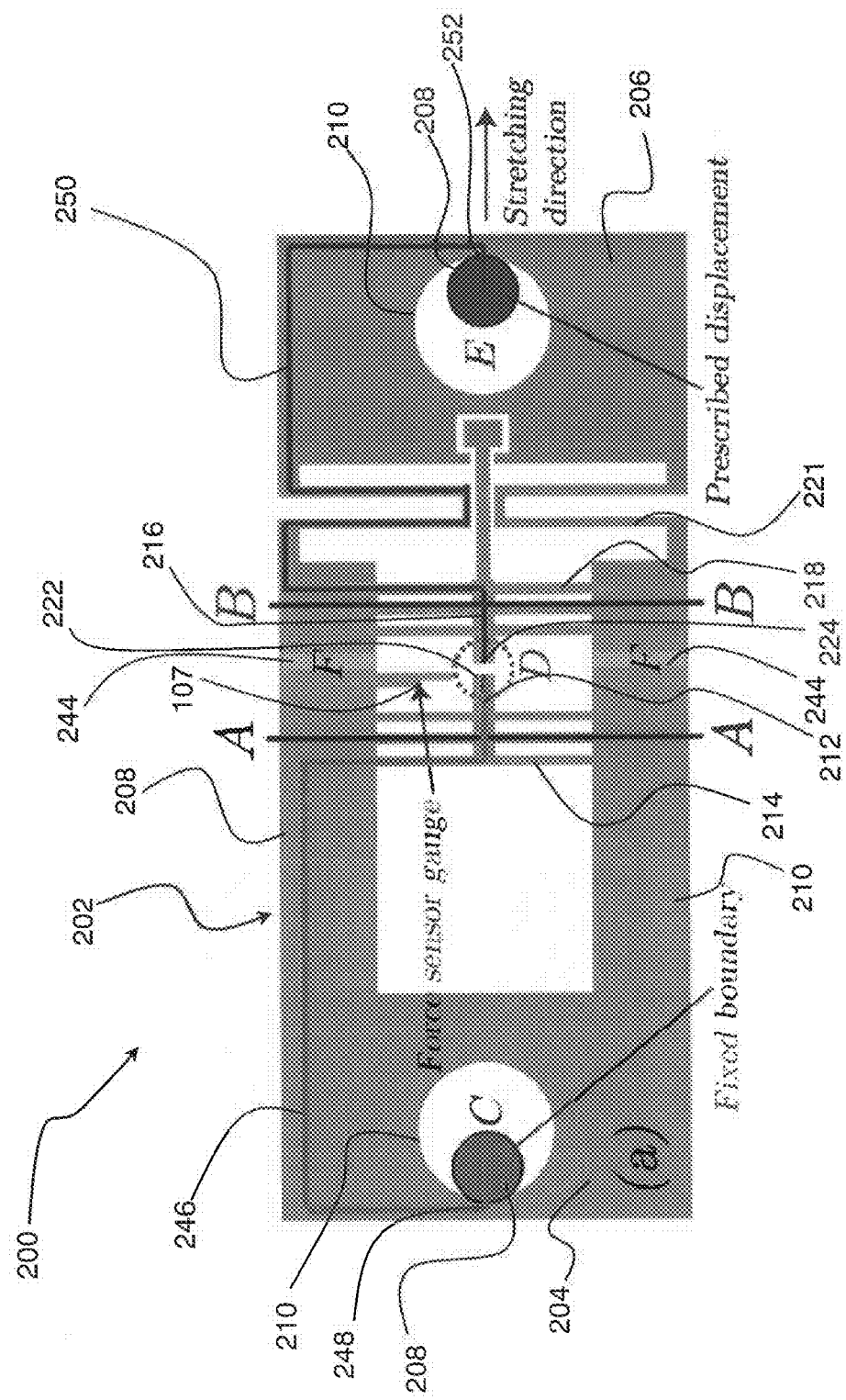
FIG. 13 shows an in situ uniaxial testing device for mechano-electrical measurements, according to an embodiment of the present invention, where lines indicate open circuit in the absence of a specimen at D.

FIG. 13 shows an example uniaxial testing stage 200 for in situ mechano-electrical testing of nanoscale and microscale samples according to an embodiment of the present invention. The testing stage 200 is made from a substrate material such as but not limited to silicon, and includes a generally rectangular frame 202 having a first opposing end 204 and a second opposing end 206. A pair of laterally opposed side beams 208, 210 extend longitudinally between the first opposing end 204 and the second opposing end 206. The testing stage 200 may be of various dimensions.

As with the stage 50, the first end 204 and the second end 206 can be coupled to a moving stage, for instance via pillars 208 of a piezoelectric actuator (labeled in FIG. 13 as C and E) coupled at apertures such as pinholes 210. For tensile testing, the first end 204 and the second end 206 are moved away from one another along a loading direction, while for compressive testing, the first end and the second end are moved toward one another along the loading direction (the direction of the arrow in FIG. 13 is for tensile testing). Either the first end 204 or the second end 206 may be a fixed end, while the other end is moved. Alternatively, both ends 204, 206 may be moved while loading.

For supporting a specimen such as the specimens 84, 130, 150, a first longitudinal beam 212 is substantially laterally centered within the frame 202 and has a central axis coaxial with the loading direction. Similar to testing stage 50, the first longitudinal beam 212 bisects one or more, and preferably several, deformable force sensor beams 214, which extend laterally between the first and second side beams 208, 210. As shown in FIG. 13, the force sensor beams 214 extend along a lateral line such as line A-A. The example testing stage 200 also includes a second laterally centered longitudinal beam 216, also having a central axis coaxial with the loading direction, and bisecting a plurality of laterally extending, generally rectangular beams 218, such as along line B-B in FIG. 13. The beams 218 provide a support structure for supporting the second longitudinal beam 216 and for reducing misalignment during loading. As with testing stage 50, more than or fewer than the three support beams 218 shown in FIG. 13 are also contemplated, and the support structure is not intended to be limited to the configuration shown. To correct misalignment between the sample 84 and the loading direction and for providing additional structural integrity to the testing stage 200, springs 221 such as U-shaped springs are provided at each lateral side (respectively) near the side beams 208, 210 or elsewhere on the testing stage.

Figure 14B:
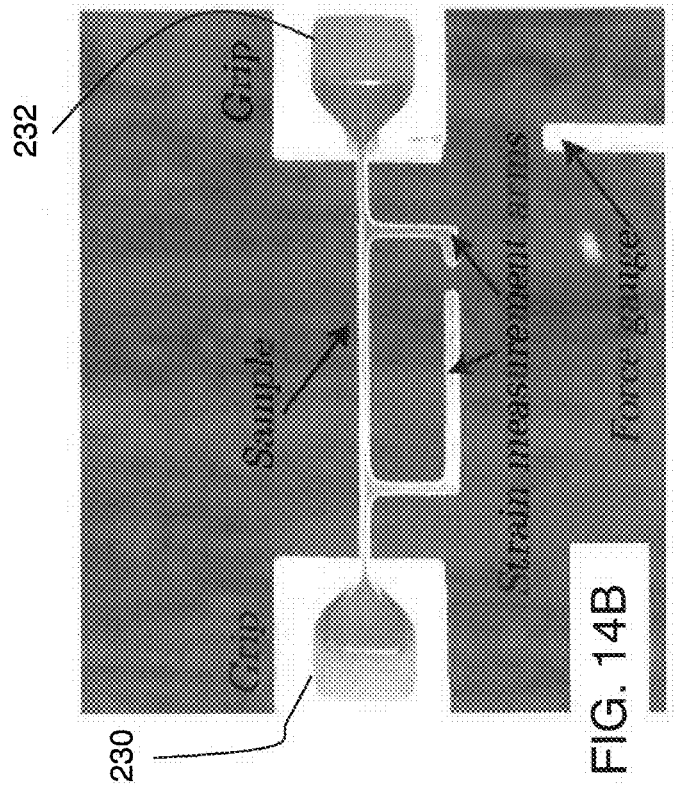
FIGS. 14A-14B show SEM images of portions of the uniaxial testing stage of FIG. 13, where
Figure 14A:
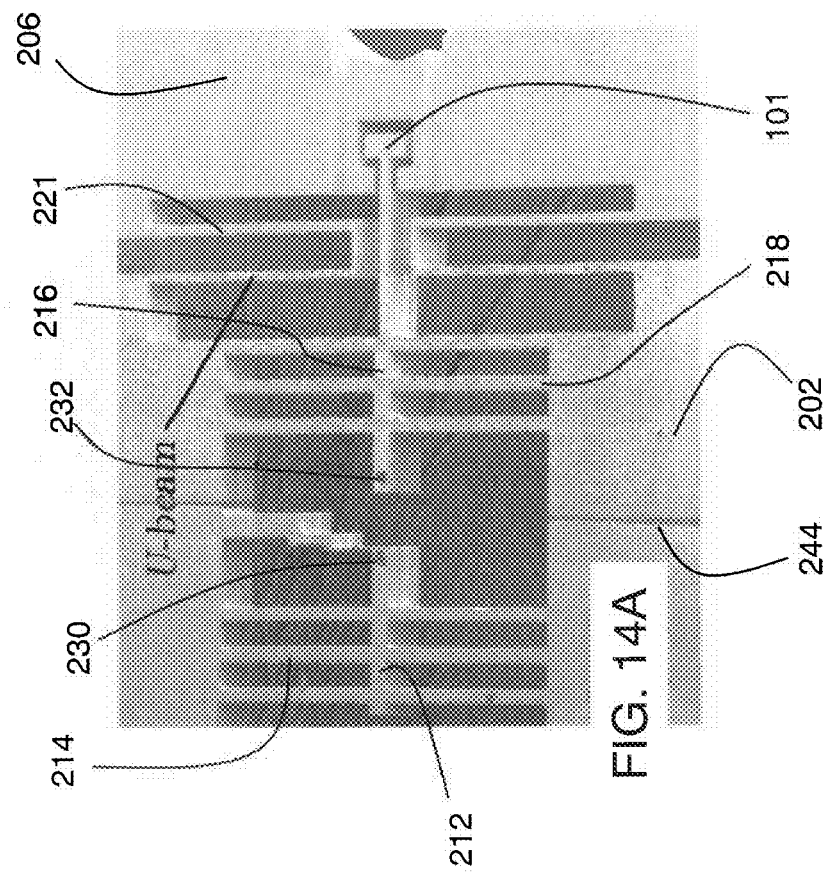

As shown in FIG. 13 and FIGS. 14A-14B, the first and second longitudinal beams 212, 216 are coaxially disposed so that free ends 222, 224 of the beams face one another, the edges of which are separated by a gap (labeled D in FIG. 13). As with the testing stage 50, these free ends 222, 224 include generally symmetrical sample slots 230, 232, which support ends of the separately fabricated sample (in FIG. 14B, a specimen similar to specimen 130 is shown by example) and provide sample grips. The grips 230, 232 allow an assembly approach, so that samples from a wide range of materials can be fabricated separately from the stage 200 and tested. The sample 84, 130, 150 may be placed within the testing stage 200 as with other methods described herein.

In an example operation, the specimen 84, 130, 150 fits into the grips 230, 232, and the specimen is loaded by deforming the stage using a piezoelectric actuator with the two metal pillars 208 (C and E). Force on the specimen 84, 130, 150 is obtained from the deformation of the force sensor beams 214, where stiffness of these beams can be calibrated by scale. Upon loading, the deformation of the force sensor beams 214 and the strain of the sample 84, 130, 150 can be obtained from image analysis.

FIGS. 15A-15H show an example fabrication procedure for the uniaxial testing stage 200, in which FIGS. 15A-15E are similar to the fabrication procedure shown in FIGS. 3A-3F. For example, as shown in FIG. 15A, Al films 110 are deposited on both sides of a silicon wafer 112, followed by a layer 114 formed by photoresist (PR) spin-coating. Then, the PR layer 114 and the Al film layers 110 are patterned by lithography (FIG. 15B) and wet etching (FIG. 15C). The patterned Al layers 110 serve as masks during an ICP-DRIE process. The silicon wafer 112 is etched from the top to make grooves 116 for the grips 230, 232 and then the bottom to release the free-standing, three-dimensional structures (FIG. 15D). After etching, the photoresist layers 114 and the Al masks 110 are removed (FIG. 15E).

Following fabrication of the Si stage, a thin layer of SiO$_2$ 240 is grown on all the surfaces (FIG. 15F). A thin, preferably ductile layer of a conductive material 242, such as but not limited to gold, is then deposited, e.g., by sputtering, which coats both horizontal and vertical surfaces of the stage (FIG. 15G). The two ends of the stage are then electrically isolated from one another by removing part of the conductive material from the mid region 244 (see line F-F in FIG. 13) of the stage 200 by FIB, as shown in FIG. 15H.

Thus, as shown in FIG. 13, the electrically conductive layer 242 provides a first conductive path 246 between a contact 248 on the stage 200 (as a nonlimiting example, where the conductive layer contacts the left (as shown) metal pillar 208) and the grip 230. Similarly, a second conductive path 250 is provided between a contact 252 on the stage 200 (where the conductive layer contacts the right (as shown by nonlimiting example) metal pillar 208) and the grip 232. The open mid region 244 creates an open circuit across the stage 200, so that the ends 204, 206, and both of the metal pillars 208 are electrically isolated from one another unless the specimen 84, 130, 150 is placed in the grips 230, 232 to close the circuit. In a nonlimiting example method, the specimen 84, 130, 150 is placed in the grips 230, 232 by using a micro manipulator. Resistance measurement and other electrical or electromechanical measurement of the specimen 84, 130, 150 can be performed by forming the closed circuit through the two metal pillars. Though contacts 248, 252 are shown in FIG. 13 to electrical contact pillars 208, it is also contemplated that other locations along the conductive layer 242 can provide contacts, and may be electrically coupled to other electrical devices, so long as the contacts are electrically isolated from one another before the circuit is closed by the specimen 84, 130, 150 (or so long as the circuit is otherwise suitably configured for measurement by the specimen closing the gap). It is also contemplated that same or separate devices may be used to mechanically manipulate the stage 200 and to provide electrical measurement for the specimen 84, 130, 150.

Figure 16:
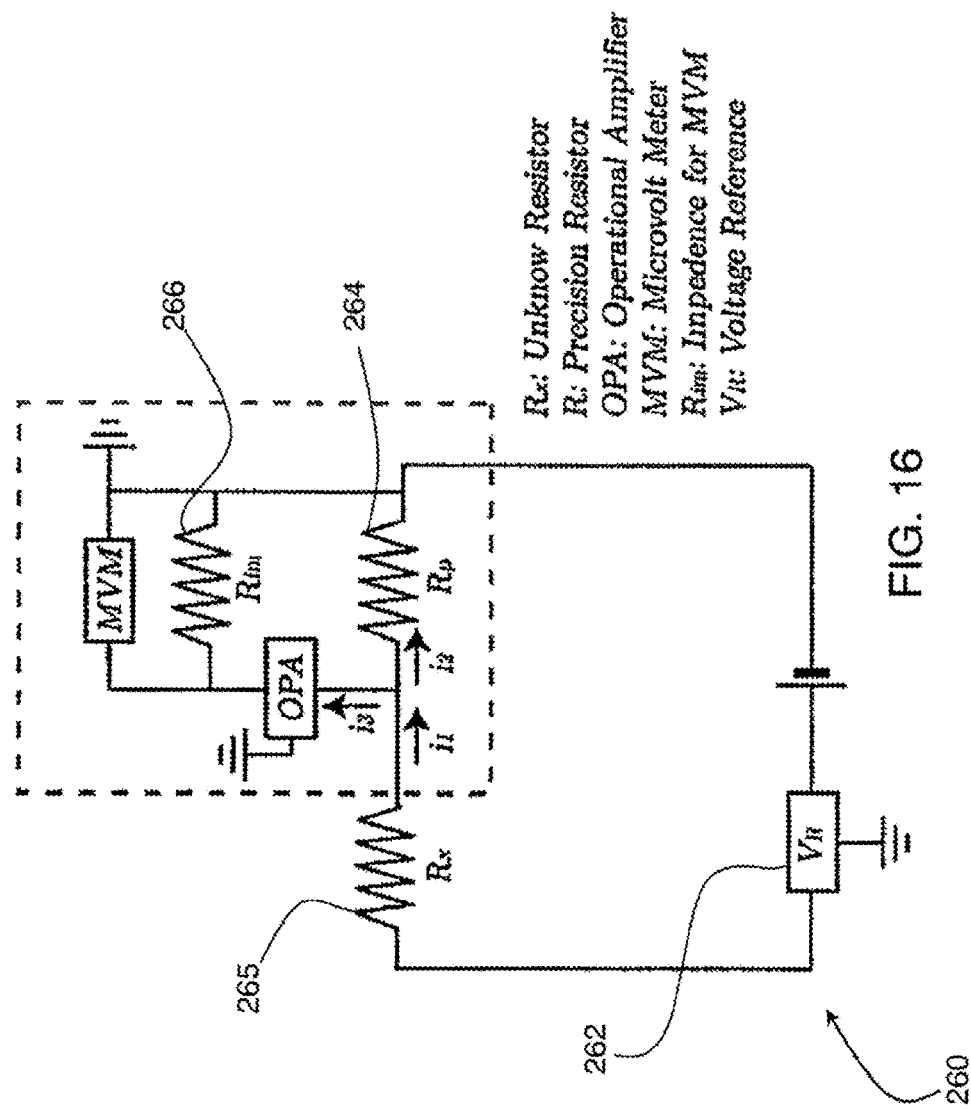
FIG. 16 shows a circuit for in situ piezoresistance measurement, according to an embodiment of the present invention.

In an example operation using the testing stage 200, mechano-electrical properties of small-scale single crystal silicon (SCS) samples (one of the most commonly used piezoresistive materials) are characterized by forming a circuit, such as a circuit 260 shown in FIG. 16. The testing stage 200 offers concurrent and direct in situ measurement of mechanical and electrical measurement of small volume specimens. With uniaxial tensile loading up to fracture of samples, stress-strain response, fracture strength, and piezoresistance can be independently and simultaneously measured. Those of ordinary skill in the art will appreciate that the example methods described herein can be readily extended to various materials and sizes due to the assembly approach.

Figure 17:
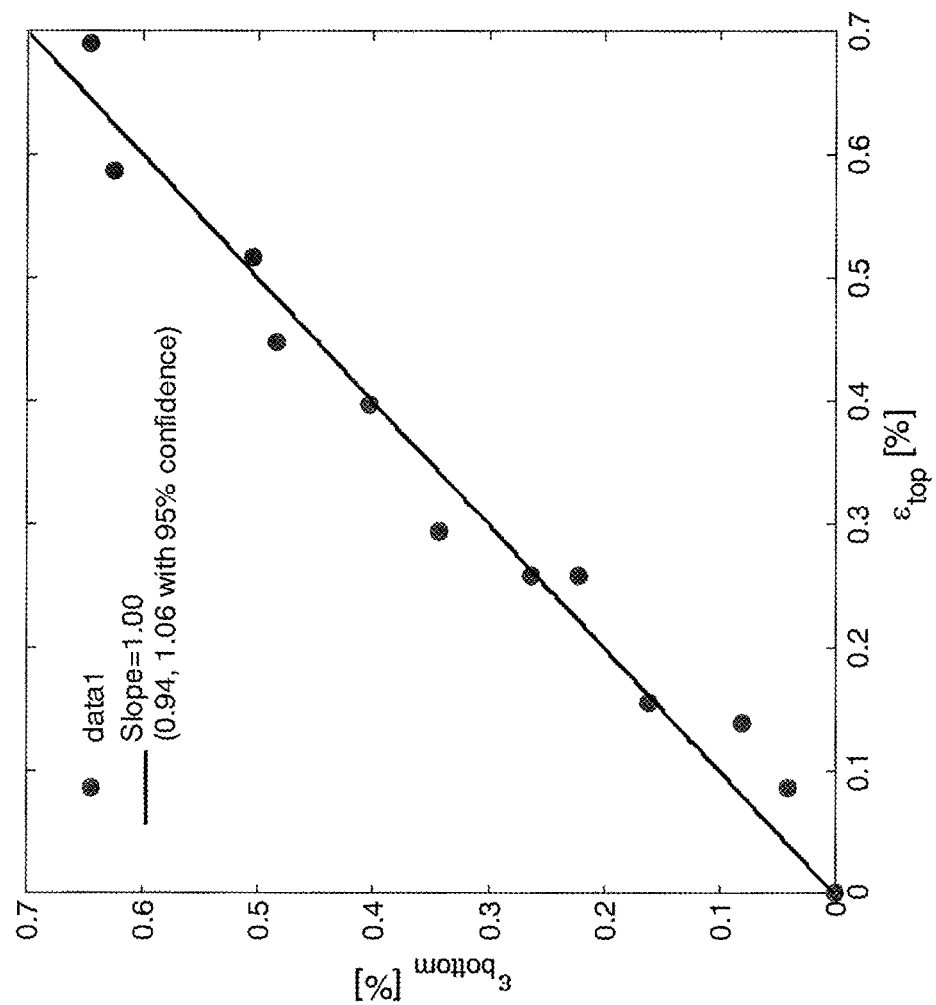
FIG. 17 shows experimental results of uniaxial loading.

In order to achieve desired uniform strain, the U-beam springs 221 and the ductile gold film 242 are used to suppress misalignment between the pillars 208 and the grips 230, 232, and between the grips and the sample, respectively. The uniform strain was confirmed by the equality of strain at the top and bottom of the specimen as shown in FIG. 17.

Contact resistance between the metal pillars 208 and the testing stage 200 was measured before the FIB cut (at midregion 244), and it was consistently less than 50Ω for all tested apparatuses. This contact resistance is ignored for all resistance measurement in the example testing operations due to the relatively large resistance of the tested samples. This assumption induces only about 0.01% measurement error, which is compatible with instrument error. Electrical isolation between the two ends 204, 206 was confirmed by comparing resistances of the stage 200 before and after the FIB cut, and the ratio between the two cases was less than $10^{-6}$. An example resistance measurement of the specimen is performed by using the circuit 260 shown in FIG. 16. In the circuit 260, a voltage reference ($V_R$) 262, a precision resistor ($R_p$) 264, and an impedance for a microvolt meter (MVM) 266 ($R_{im}$) are precisely known. The total resistance for the measurement instrument indicated by the dotted line in FIG. 16 is $$R_t = \frac{R_p R_{im}}{R_p + R_{im}} \approx R_p$$

where $R_{im} \gg R_p$. Therefore, the current in the circuit 260 satisfies $i_1 = i_2 + i_3 \approx i_2$. Finally, the unknown resistance, $R_x$, can be obtained by $$R_x = R_p \left( \frac{V_R - V_p}{V_p} \right)$$

where $V_p$ is measured voltage at the precision resistor ($R_p$) 264. The resistance measurement instrument was calibrated by measuring known resistance of a precision resistor, which verified 99.99% accuracy measurement.

Figure 18:
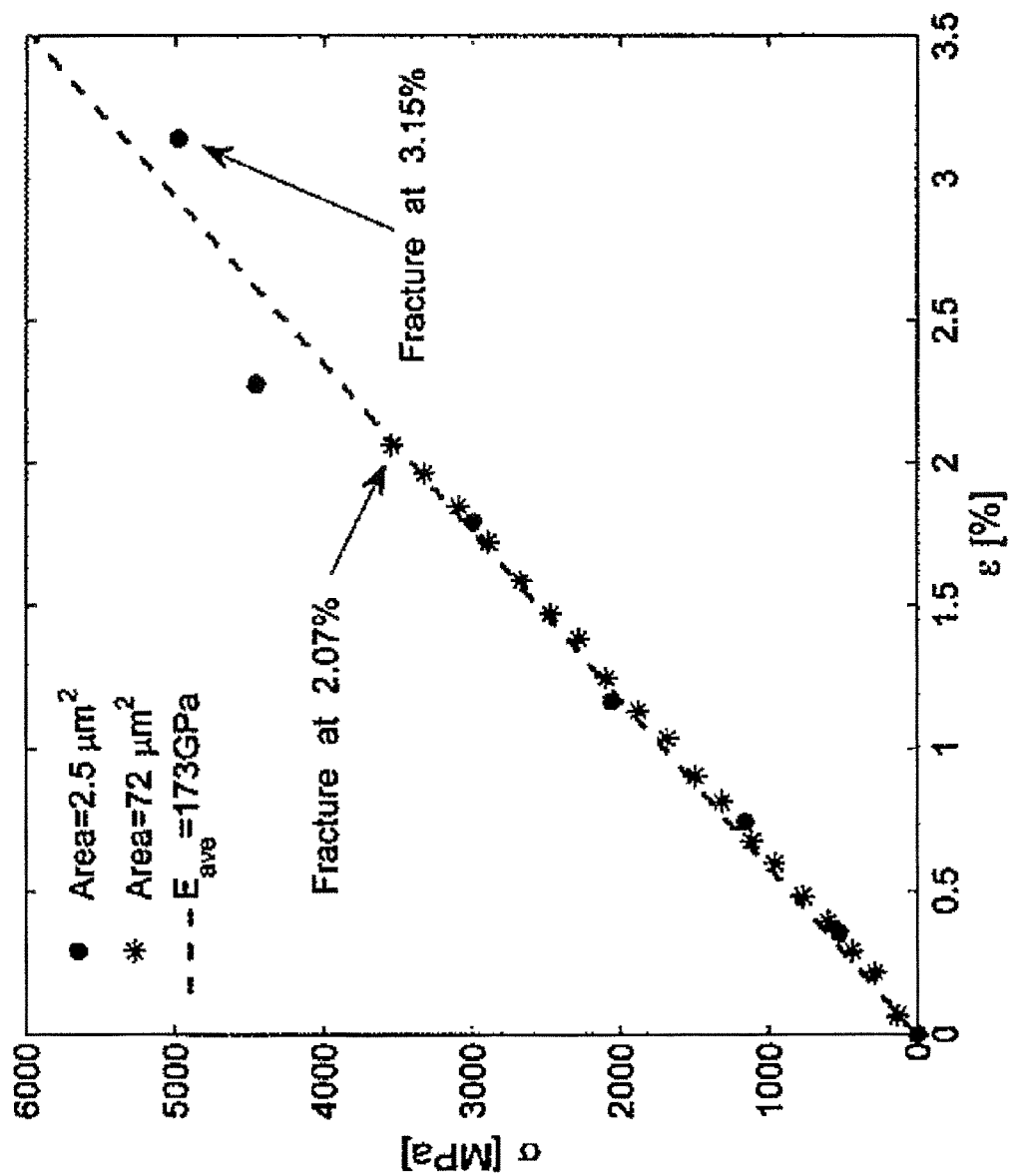
FIG. 18 shows experimental results of uniaxial loading and fracture strength.

The single crystal silicon specimens were separately fabricated by ICP-DRIE and characterized. Stress-strain response, fracture strength, and piezoresistance were independently and simultaneously measured. FIG. 18 shows the stress-strain response of two SCS samples with cross-sectional areas of 72 μm² and 2.5 μm². The elastic modulus of both the samples is 173 GPa, close to the expected value of 169 GPa for SCS along <110> direction. Two samples show substantial difference in the fracture strain, 2.07% and 3.18% for the larger and the smaller samples, respectively.

Figure 19:
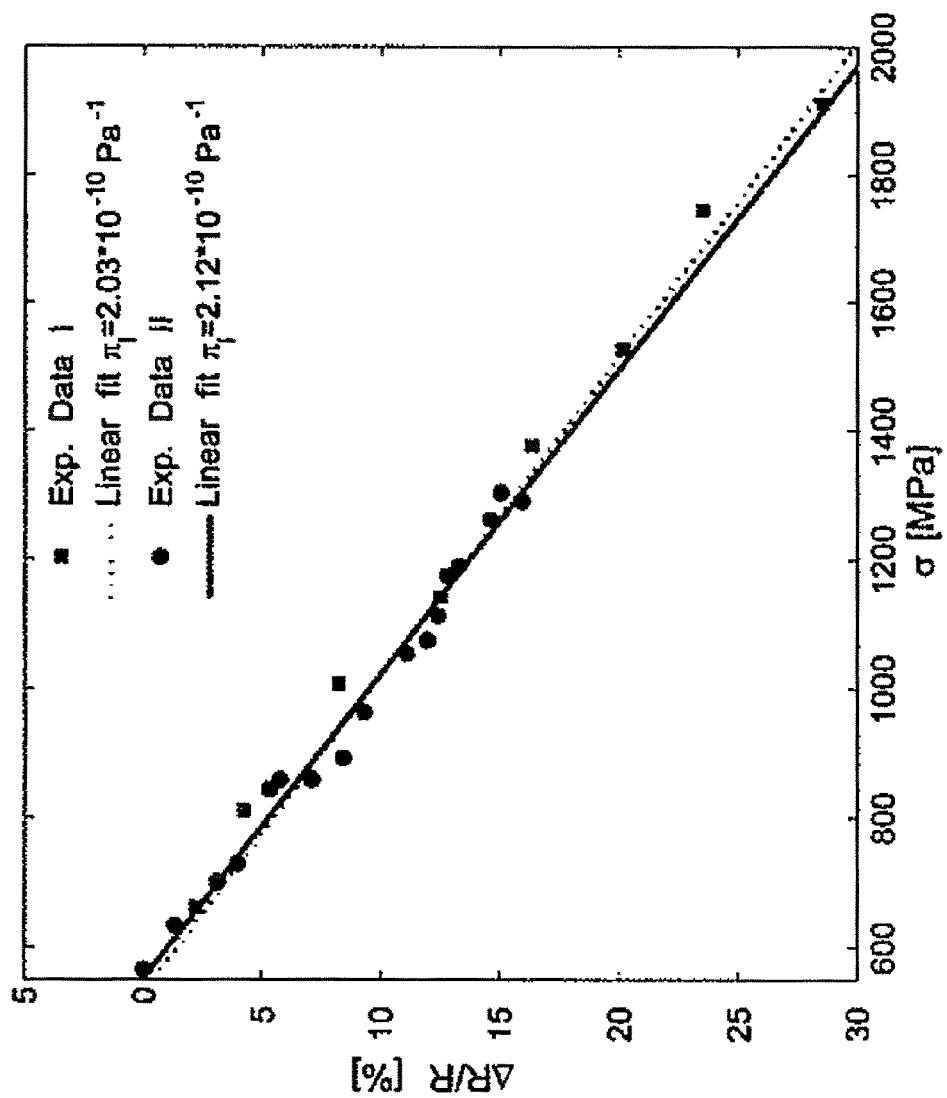
FIG. 19 shows experimental results of piezoresistivity-stress measurement.

FIG. 19 shows piezoresistance measurement from two independent specimens and stages. Due to the uniaxial loading, the resistance change is given by $$\frac{\Delta R}{R} = \pi_1 \sigma_1$$

where $\pi_1$ and $\sigma_1$ are the longitudinal piezoresistance coefficient and stress, respectively. Using the above equation, piezoresistance coefficients ($\approx 2 \times 10^{-10}$ Pa$^{-10}$) are obtained and they agree not only with each other, but also with previously reported data.

Other embodiments of the present invention provide, among other things, in situ uniaxial testing apparatus in scanning and transmission electron microscopy (SEM and TEM) at high temperature for microscale and nanoscale samples. While methods have been provided to test some small volume materials at room temperature, microscale and nanoscale devices are often required to operate in a wide range of temperature, such as (but not limited to) sensors used in automobiles, planes, and aerospace. Hence, it is very useful to test and understand material properties of such materials at in-service temperature, including in high temperature environments.

Figure 20:
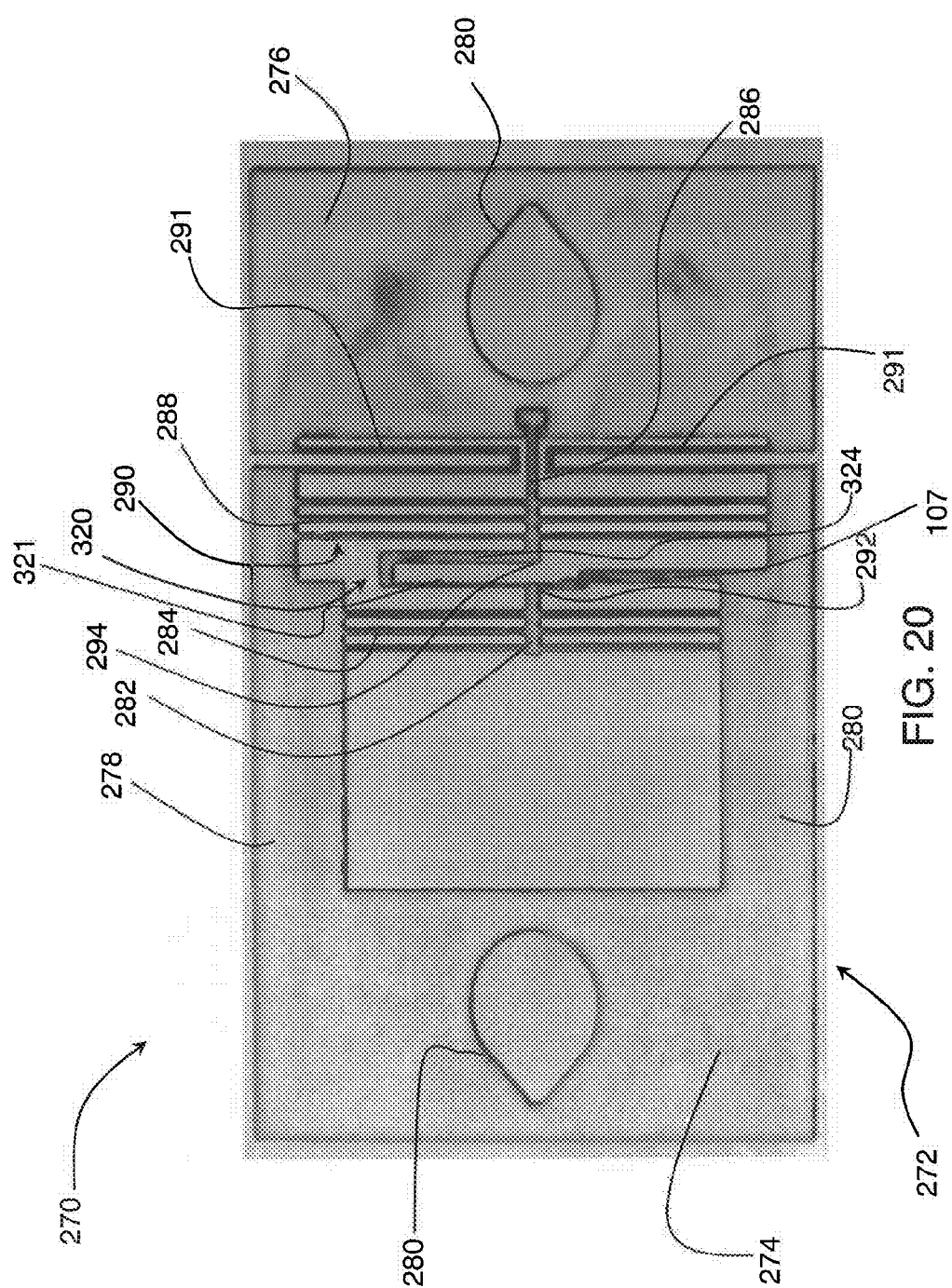
FIG. 20 shows a silicon carbide (SiC) based MEMS stage for uniaxial material test of microscale/nanoscale samples, according to an embodiment of the present invention.
Figure 21:
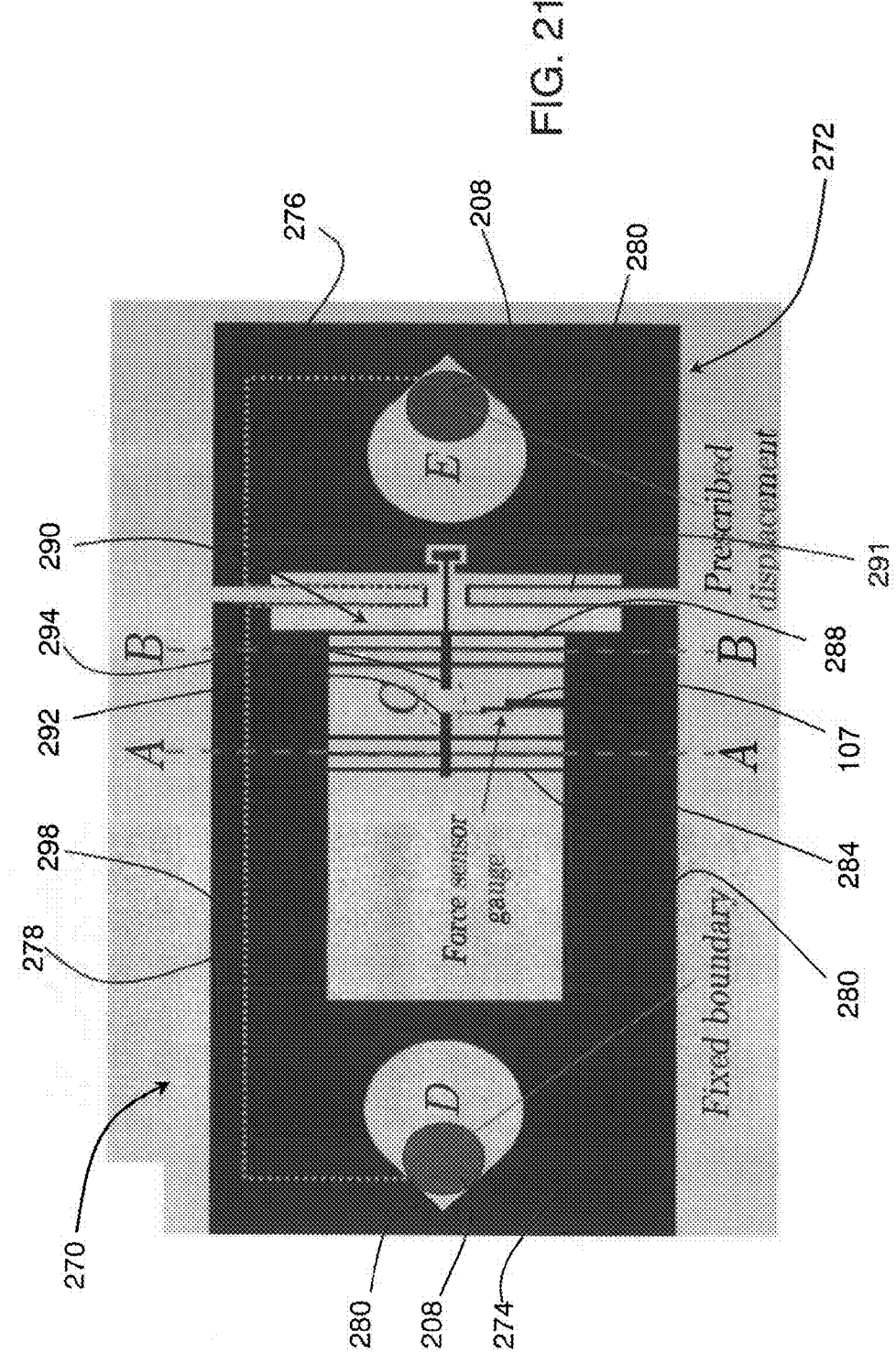
FIG. 21 shows example components of the SiC based MEMS stage of FIG. 20.

To provide uniaxial testing of nanoscale to microscale samples at high temperature (as a nonlimiting example, at or above about 1000° C.), a high-temperature testing stage is provided according to another embodiment of the present invention. An example silicon carbide (SiC) based MEMS testing stage 270 is shown in FIGS. 20 and 21. Silicon carbide is chosen as an example material for the example testing stage 270 due to its outstanding mechanical properties at high temperature, semiconductive characteristics, and high heat conductive coefficient. For example, SiC has high melting temperature (2730° C.) and shows small variation in elastic modulus (within 4% between at 1000° C. with respect to room temperature). However, other materials for high-temperature testing stages are also contemplated, such as Nichrome, platinum, or others. Choice of particular material can be at least partially based, as a nonlimiting example, on mechanical properties of the material at particular target high temperatures. The melting temperature and temperature range for small variation in elastic modulus for particular materials can be selected according to the testing needs, such as the particular environment in which a particular sample material will be use. Also, while the semiconductive characteristics of SiC are useful for a testing stage such as stage 270, it is not required that all high-temperature compliant testing stages be made from material having such characteristics.

The testing stage 270, e.g., made entirely from SiC substrate material, includes a generally rectangular frame 272 having a first opposing end 274 and a second opposing end 276. A pair of laterally opposed side beams 278, 280 extend longitudinally between the first opposing end 274 and the second opposing end 276. The testing stage 270 may be of various dimensions.

As with the stages 50, 250 the first end 274 and the second end 276 can be coupled to a moving stage, for instance via pillars 208 of a piezoelectric actuator (labeled in FIG. 21 as D and E) coupled at apertures such as pinholes 280. For tensile testing, the first end 274 and the second end 276 are moved away from one another along a loading direction as with stages 50, 250, while for compressive testing, the first end and the second end are moved toward one another along the loading direction. Either the first end 274 or the second end 276 may be a fixed end, while the other end is moved. Alternatively, both ends 274, 276 may be moved while loading.

For supporting a specimen such as the specimens 84, 130, 150, a first longitudinal beam 282 is substantially laterally centered within the frame 202 and having a central axis coaxial with the loading direction. Similar to testing stages 50, 250 the first longitudinal beam 282 bisects one or more, and preferably several, deformable force sensor beams 284, which extend laterally between the first and second side beams 278, 280. As shown in FIG. 21, the force sensor beams 284 extend along a lateral line such as line A-A. The example testing stage 270 also includes a second laterally centered longitudinal beam 286, also having a central axis coaxial with the loading direction, and bisecting a plurality of laterally extending, generally rectangular beams 288, such as along line B-B in FIG. 21. The beams 288 provide a support structure 290 for supporting the second longitudinal beam 286 and for reducing misalignment during loading. As with testing stages 50, 250 more than or fewer than the three support beams 288 shown in FIGS. 20-21 are also contemplated, and the support structure 290 is not intended to be limited to the configuration shown. To correct misalignment between the sample 84, 130, 150 and the loading direction and for providing additional structural integrity to the testing stage 270, springs 291 such as U-shaped springs are provided at each lateral side (respectively) near the side beams 278, 280 or elsewhere on the testing stage.

The first and second longitudinal beams 282, 286 are coaxially disposed so that free ends 292, 294 of the beams face one another, the edges of which are separated by a gap 296 (labeled C in FIG. 21). As with the testing stages 50, 250 these free ends 292, 294 include generally symmetrical sample slots, which support ends of the separately fabricated sample and provide sample grips, such as those shown in FIGS. 2A-2B, FIGS. 5A-5D, and/or FIGS. 14A-14B. The grips, as with those of stages 50, 250, allow an assembly approach, so that samples from a wide range of materials can be fabricated separately from the stage 270 and tested. The sample 84, 130, 150 may be placed within the testing stage 270 as with other methods described herein.

The configuration of the example high-temperature testing stage 270 and the high-temperature material (e.g., SiC) allow simultaneous force measurement by measuring deformation of the force sensor beams 284 at a raised temperature (as a nonlimiting example, about 1200° C.). Further, because SiC is a semiconductive material, the example stage 270 can be resistively heated by applying electric current through contacts D-E (FIG. 21). SiC also has a high heat conductive coefficient, and thus can be transferred to the specimen 84, 130, 150 efficiently.

Figures 23A, 23B:
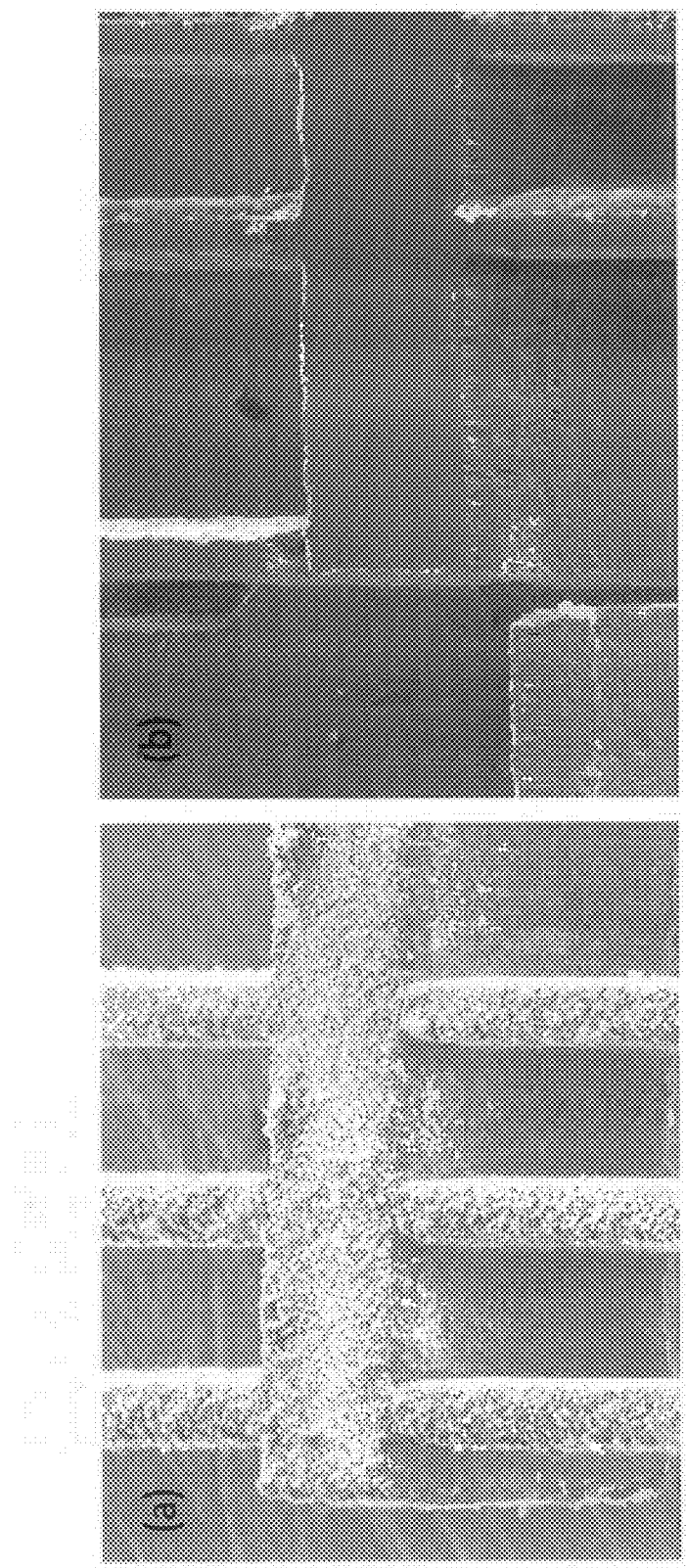
FIGS. 23A-23B show surface roughness in an example SiC based MEMS stage before and after HF cleaning, respectively.
Figure 24B:
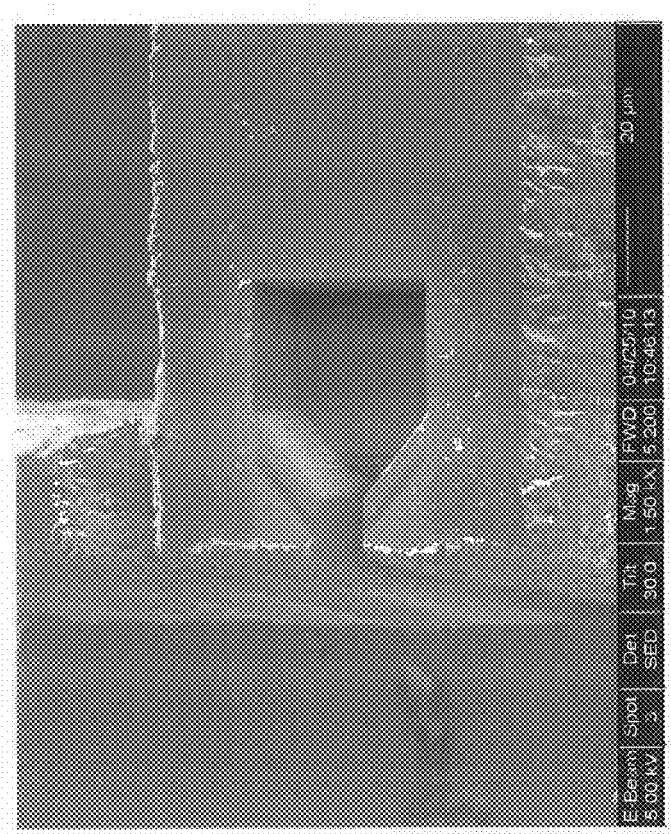
FIGS. 24A-24B show SEM images of an example SiC stage, where
Figure 24A:
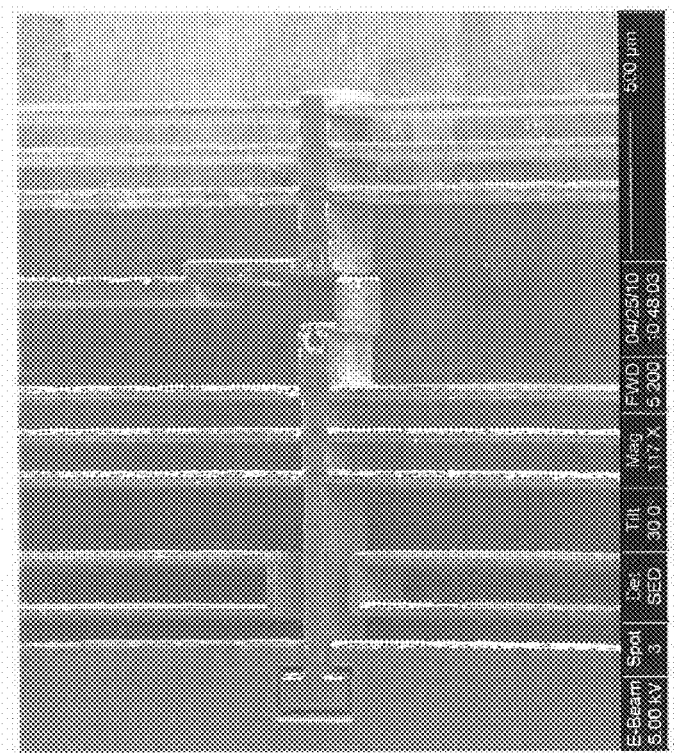

FIGS. 22A-22D show an example fabrication method for the SiC testing stage 250. An SiC substrate 300, shown in FIG. 22A, is provided, and a frame structure for the testing stage 250 is fabricated by laser milling (FIG. 22B). Then, debris 302 deposited on the SiC stage during laser milling is removed by HF wet etching, as shown in FIG. 22C. FIG. 23A shows a portion of an example SiC testing stage before I-IF wet etching, and FIG. 23B shows a portion after HF wet etching. A groove 304 for the grips is then created by ion beam milling (FIG. 22D). Alternatively, the stage 270 can be fabricated by ICP-DRIE. It will be appreciated that features disclosed for particular stages provided herein, such as markers, can be applied to any or all stages herein. FIGS. 24A-24B show a completed SIC stage in SEM.

In an example embodiment, the testing stage 270 includes a bi-material type temperature sensor 320 for evaluating temperature in situ. As shown in FIGS. 20 and 25A-25E, the temperature sensor 320 includes a measuring arm 321, which may be directly supported by a substrate 322 (such as a portion of the testing stage 270 or a different stage) or indirectly supported by a support 323, depending on the particular configuration used. Another arm 324 includes an end 326 generally facing the free end of the measuring arm, serving as a gauge or reference, and this arm may itself be directly or indirectly supported by the testing stage 270 or a different stage, depending on the particular configuration used. In other embodiments, the measuring arm 321, the substrate 322, the support 323, and the reference arm 324 may be a single piece, which itself is attached to the testing stage 270 or a different stage. Preferably, the measuring arm 321, the reference arm 324, and the support 323 are of a unitary material, which may be that of the testing stage or of a different material. Further, the arms 321 and 324 can extend from a portion of the testing stage 270 (or a different stage). In FIG. 20, the arms 321 and 324 extend from the longitudinal beams 282, 286, respectively, though the arms may extend from other portions of the testing stage in other embodiments, or may be part of a unitary piece, as discussed above, that is attached to the testing stage 270 (or a different stage) at any of various locations.

Figures 25A, 25B, 25C, 25D, 25E:
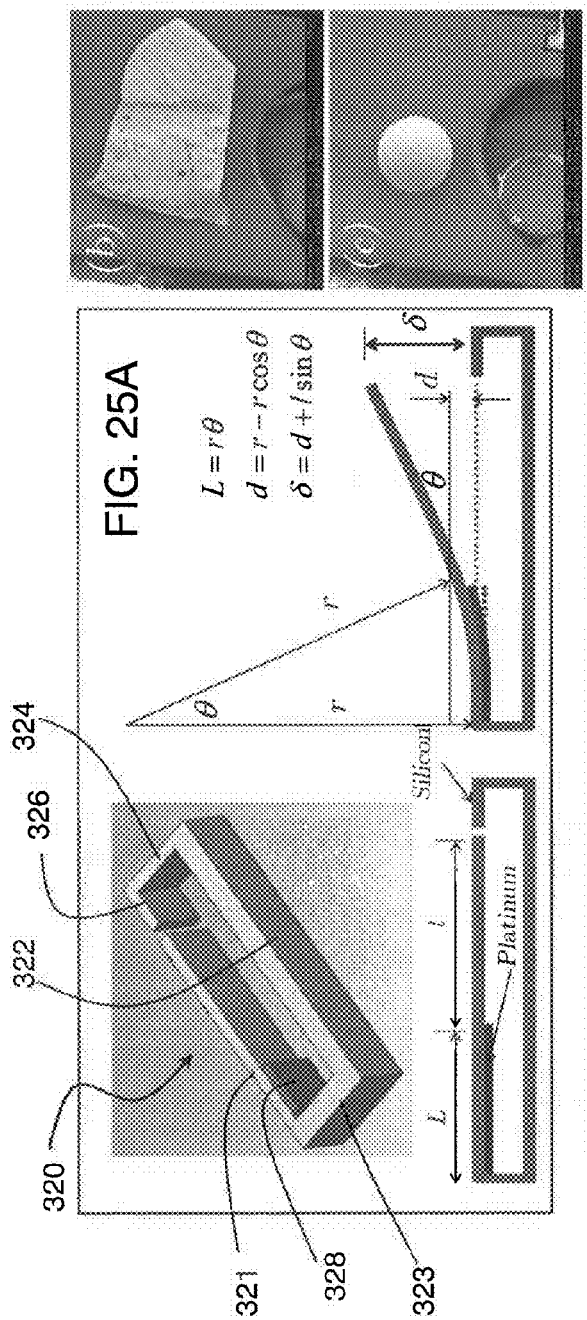
FIG. 25A schematically shows a bi-metal type temperature sensor.
FIGS. 25B-25C show in situ in SEM solid-to-liquid phase transition for Pb solder.
FIGS. 25D-25E show a Si—Pt based temperature sensor on an SiC stage, where δ increases with increase in temperature due to thermal expansion coefficient mismatch.

The measuring arm 321 includes an additional layer 328 of a material having a different thermal expansion coefficient than that of the principal layer of the measuring arm, thus providing a bi-material temperature sensor. As shown in the example of FIG. 25A, the measuring arm 321 (as well as the arm 324) is made of silicon, while the additional layer 328 is platinum. In another nonlimiting example embodiment, the materials are SiC and platinum, respectively. Si+Pt may be useful, for instance, at relatively low temperatures (e.g., below 600° C. or below brittle-to-ductile transition temperature for silicon). The measuring arm is thus divided into two lengths: a length L along both layered materials, and a length l, where the measuring arm has one layer of material. A distance $\delta$ can be defined between the free end of the measuring arm 321 and the end of the reference arm 324. This distance $\delta$ increases with increase in temperature due to the thermal expansion coefficient mismatch. To calibrate the temperature sensor 320, the onset of phase transition for pure metals such as (but not limited to) Ti, Zn, Al, and Ag with known melting temperatures can be correlated with $\delta$. General principles of the bi-metal temperature sensor 320 can be found in S. Timoshenko, "Analysis of bi-metal thermostats," Journal of the Optical Society of America, 11(3): 233-255, 1925, which is incorporated in its entirety by reference herein.

Figure 26A:
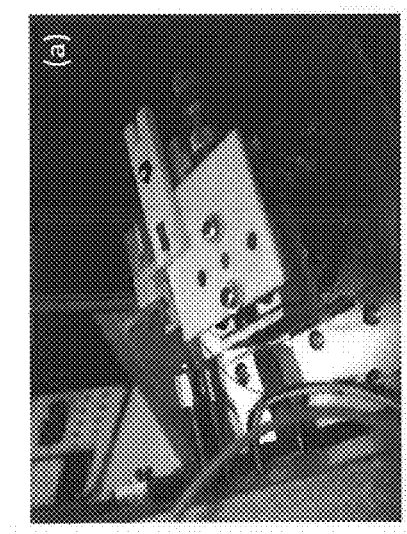
FIGS. 26A-26C show an example experimental arrangement, where
Figure 26B:
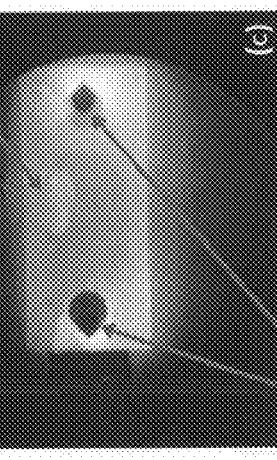
Figure 26C:
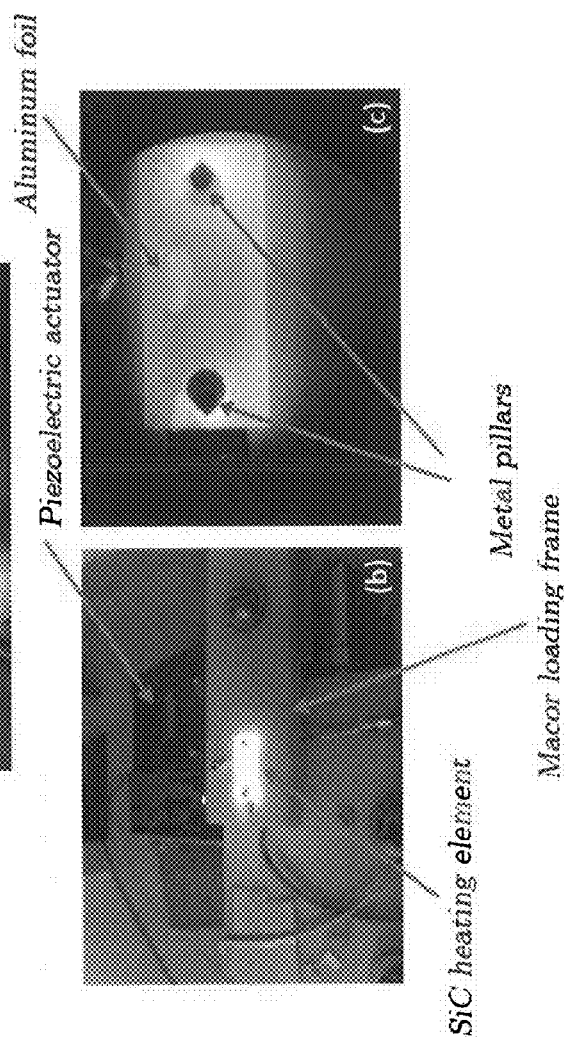
Figure 27A:
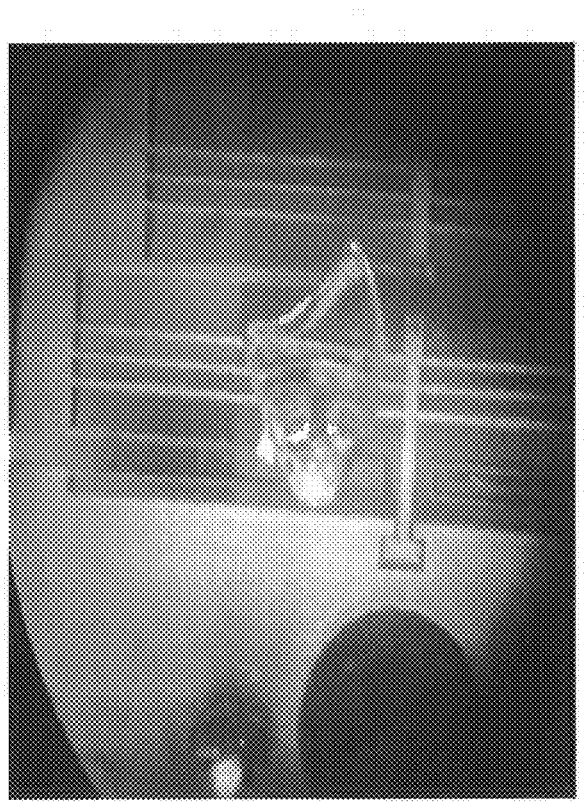
FIGS. 27A-27B show an example SiC based MEMS stage at high temperature (glass melting temperature) in a vacuum chamber.
Figure 27B:
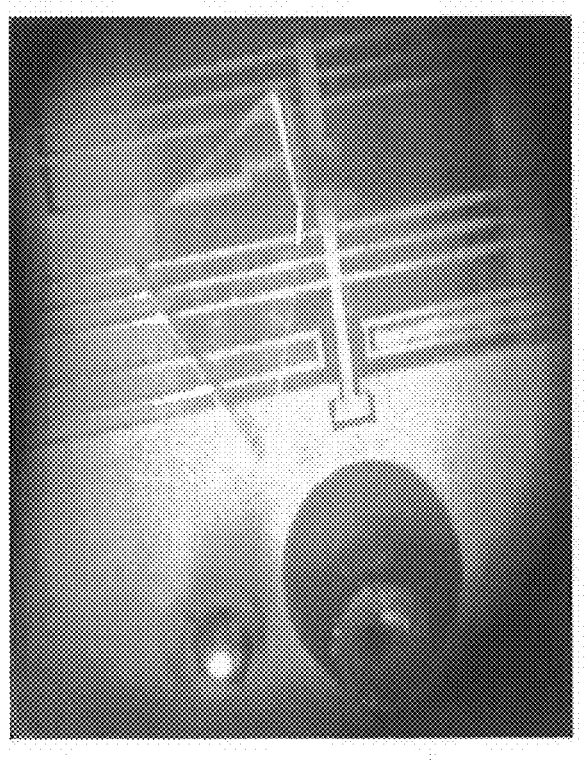

For uniaxial testing, the testing stage 270 can be operated as discussed herein with respect to other testing stages. In example methods using the testing stage 270, mechanical characterization can be performed by recovering known elastic modulus of single crystal silicon samples at room temperature. Then, the bi-material type temperature sensor can be calibrated as described above. FIGS. 26A-26C show an example operation demonstrating heating capability by using an SiC heating element in air. An Si stage is placed on a piezoactuator (FIG. 26A), and heat radiation is provided by applying electric current (FIGS. 26B-26C) through the stage, such as through resistive path 298 (FIG. 21) along the frame 272 between pillars 208. The temperature is believed to have reached about 1200° C. FIGS. 27A-27B show the testing stage 270 in a vacuum chamber, demonstrating the testing stage operating at glass melting temperature.

The size of the example SiC stage 270 is small enough to localize influence of heat near interested samples without damaging SEM/TEM, and thus in situ testing of microscale or nanoscale samples 84, 130, 150 in an SEM/TEM environment can be performed. Such in situ uniaxial testing allows direct observation of fundamental mechanisms of microscale or nanoscale samples. This capability can provide opportunities not only to study MEMS/NEMS related materials with temperature variation, but also to explore energy related materials that are used in nuclear reactors and fossil-fired plants, for instance, at high temperature. Efficiency of the nuclear and fossil-fired plants is directly related to their operation temperature. For example, nuclear reactors generally operate at 330° C. with 34% efficiency, while the efficiency will be 50% at 1000° C. This clearly indicates the importance of providing advanced materials for higher temperature applications and a material testing method at in-service temperature. By using the example SiC based stage 270, underlying mechanisms in material degradation, creep, and crack formation processes at high temperature can be directly observed in situ in SEM/TEM. This fundamental understanding of material responses at high temperature will provide materials design criteria for desired material properties and reliable life-span prediction.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. A microscale testing stage comprising:
   a frame having first and second opposing ends and first and second side beams;
   at least one deformable force sensor beam near the first end extending laterally across said frame between the first and second side beams;
   a first longitudinal beam bisecting said at least one force sensor beam and having a free end;
   a second longitudinal beam having a free end facing the free end of said first longitudinal beam to define a gap therebetween;
   a support structure disposed near the second end;
   a pair of slots disposed at each of the free ends of the first and second longitudinal beams, respectively; and
   a separately fabricated microscale or nanoscale specimen, said specimen comprising:
      a central gauge length portion of a material to be tested;
      first hinges disposed at each of opposing longitudinal sides of said gauge length portion;
      second hinges disposed at each of opposing longitudinal sides of said first hinges, wherein said first hinges are disposed between said second hinges and said gauge length portion, said first hinges and said second hinges providing a self-aligning mechanism for uniaxial loading; and
      opposing ends for inserting into each of the pair of slots, respectively.

2. The testing stage of claim 1, wherein each of said first hinges and said second hinges are configured to have a high bending stiffness along a predetermined direction and a lower bending stiffness along other directions.

3. The testing stage of claim 2, wherein the predetermined direction for said first hinges is substantially perpendicular to said predetermined direction for said second hinges.

4. The testing stage of claim 1, wherein cross-sectional areas of each of said first hinges and said second hinges are larger than a cross-sectional area of said gauge length portion.

5. The testing stage of claim 4, wherein a bending stiffness of each of said first hinges and said second hinges is much smaller than a bending stiffness of said gauge length portion along a predetermined direction.

6. The testing stage of claim 1, wherein each of said pair of slots has a depth within said frame that is about half a thickness of said stage.

7. The testing stage of claim 1, wherein said specimen further comprises:
   a pair of opposed measurement arms supported by said specimen, each of said pair of opposed measurement arms including a portion extending parallel to a length of said specimen and providing a measurement gauge.

8. The testing stage of claim 1, wherein said support structure comprises a plurality of laterally extending beams between said first and second side beams, said second longitudinal beam bisecting said laterally extending beams.

* * * * *